(12) United States Patent
Murata et al.

(10) Patent No.: US 10,076,243 B2
(45) Date of Patent: Sep. 18, 2018

(54) OPHTHALMIC IMAGING DEVICE

(71) Applicant: NIDEK CO., LTD., Gamagori, Aichi (JP)

(72) Inventors: Keiji Murata, Gamagori (JP); Masaaki Hanebuchi, Nukata (JP); Masakazu Endo, Okazaki (JP)

(73) Assignee: NIDEK CO., LTD., Aichi (JP)

( * ) Notice: Subject to any disclaimer, the term of this patent is extended or adjusted under 35 U.S.C. 154(b) by 160 days.

(21) Appl. No.: 15/141,973

(22) Filed: Apr. 29, 2016

(65) Prior Publication Data

US 2016/0317028 A1    Nov. 3, 2016

(30) Foreign Application Priority Data

May 1, 2015   (JP) ................................. 2015-094468

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/0025* (2013.01); *A61B 3/1025* (2013.01); *A61B 3/117* (2013.01); *A61B 3/1225* (2013.01)

(58) Field of Classification Search
CPC ..... A61B 3/102; A61B 3/0025; A61B 3/1225; A61B 3/1025; A61B 3/0058; A61B 3/14;
(Continued)

(56) References Cited

U.S. PATENT DOCUMENTS 7,980,696 B1    7/2011  Taki et al.
2007/0076217 A1   4/2007  Baker et al.
(Continued)

FOREIGN PATENT DOCUMENTS

CN    103251382 A    8/2013
CN    102438505 B    10/2013
(Continued)

OTHER PUBLICATIONS

Oct. 7, 2016 Search Report issued in European Patent Application No. 16167642.4.

*Primary Examiner* — Brandi Thomas
(74) *Attorney, Agent, or Firm* — Oliff PLC

(57) ABSTRACT

An ophthalmic imaging device for capturing a tomographic image of an eye, includes: an OCT optical system detecting interference of reference light and measurement light; a measurement optical system including an optical scanner and an objective optical system, the optical scanner being configured to deflect the measurement light to perform scanning with the measurement light; a driver configured to displace a relative position of the optical scanner with respect to the objective optical system in an optical axis direction; and a controller configured to control the driver to adjust a turning position of the measurement light in the optical axis direction. The controller changes the turning position between a first position corresponding to a first depth band of the eye and a second position corresponding to a second depth band of the eye which is different from the first depth band.

19 Claims, 13 Drawing Sheets

(51) Int. Cl.
  *A61B 3/117* (2006.01)
  *A61B 3/12* (2006.01)
  *A61B 3/00* (2006.01)

(58) Field of Classification Search
  CPC .. A61B 3/117; G01B 9/0203; G01B 9/02089;
              G01B 9/02091; G01B 9/02044; G01B
              9/02064; G01B 9/02087; G01B 9/02077;
                                        G01B 9/02085
  USPC ........ 351/200, 203, 205, 206, 209–211, 221,
                                        351/222, 243–246
  See application file for complete search history.

(56)        References Cited

U.S. PATENT DOCUMENTS

| | | |
|---|---|---|
| 2011/0102802 A1 | 5/2011 | Izatt et al. |
| 2013/0250237 A1* | 9/2013 | Ueno .................. A61B 3/0058 351/206 |
| 2014/0098345 A1 | 4/2014 | Cai et al. |
| 2015/0077708 A1 | 3/2015 | Hauger et al. |

FOREIGN PATENT DOCUMENTS

| | | | |
|---|---|---|---|
| CN | 103989453 A | 8/2014 | |
| CN | 203885475 U | 10/2014 | |
| JP | 2011-147609 A | 8/2011 | |
| WO | 2011/050249 A1 | 4/2011 | |

* cited by examiner

OPHTHALMIC IMAGING DEVICE

CROSS REFERENCE TO RELATED APPLICATION

This application is based upon and claims the benefit of priority of Japanese Patent Application No. 2015-094468 filed on May 1, 2015, the contents of which are incorporated herein by reference in its entirety.

BACKGROUND

The present disclosure relates to an ophthalmic imaging device that captures a tomographic image of an eye.

Optical coherence tomography (OCT) has been known as a device that captures a tomographic image of an object to be examined.

In addition, in the ophthalmic field, there has recently been an attempt to obtain tomographic images of two or more portions (for example, an anterior ocular segment, a fundus, and the like) having different depth bands in an eye, by one device. For example, JP-A-2011-147609 discloses a device that performs image capturing of an anterior ocular segment and image capturing of a fundus by switching therebetween in accordance with the attachment and detachment of a lens attachment to and from an inspection window.

SUMMARY

However, in the above-mentioned technique disclosed in JP-A-2011-147609, in a case where a depth band to be captured is changed between an anterior ocular segment and a fundus, it is necessary to attach and detach an attachment, which leads to troublesomeness.

This disclosure is contrived in view of such situations, and a technical problem thereof is to provide a new ophthalmic imaging device capable of satisfactorily obtaining tomographic images of two or more portions having different depth bands in an eye.

An aspect of the present disclosure provides the following arrangements:

An ophthalmic imaging device for capturing a tomographic image of an eye, the ophthalmic imaging device comprising:

an OCT optical system including a photodetector configured to detect interference of reference light and measurement light with which the eye is irradiated;

a measurement optical system including an optical scanner and an objective optical system, the optical scanner being configured to deflect the measurement light emitted from the OCT optical system to perform scanning with the measurement light, and the objective optical system being disposed between the optical scanner and the eye and configured to guide the measurement light deflected by the optical scanner to the eye;

a driver configured to displace a relative position of the optical scanner with respect to the objective optical system in an optical axis direction; and a controller configured to control the driver to adjust a turning position of the measurement light in the optical axis direction, wherein the controller changes the turning position between a first position corresponding to a first depth band of the eye and a second position corresponding to a second depth band of the eye which is different from the first depth band.

DESCRIPTION OF ILLUSTRATIVE EMBODIMENTS

Hereinafter, typical embodiments in the present disclosure will be described with reference to the accompanying drawings. First, a first embodiment will be described with reference to FIGS. 1A to 4. An optical coherence tomography 1 (hereinafter, referred to as an "OCT device 1") according to the first embodiment is an ophthalmic imaging device that acquires depth information of an eye E to be examined. The OCT device 1 may be, for example, Fourier domain optical coherence tomography (FD-OCT) or may be time domain OCT (TD-OCT). Spectral domain OCT (SD-OCT) and wavelength swept source OCT (SS-OCT) are representative of the FD-OCT, and the present disclosure can be applied to these devices.

Figure 1A:
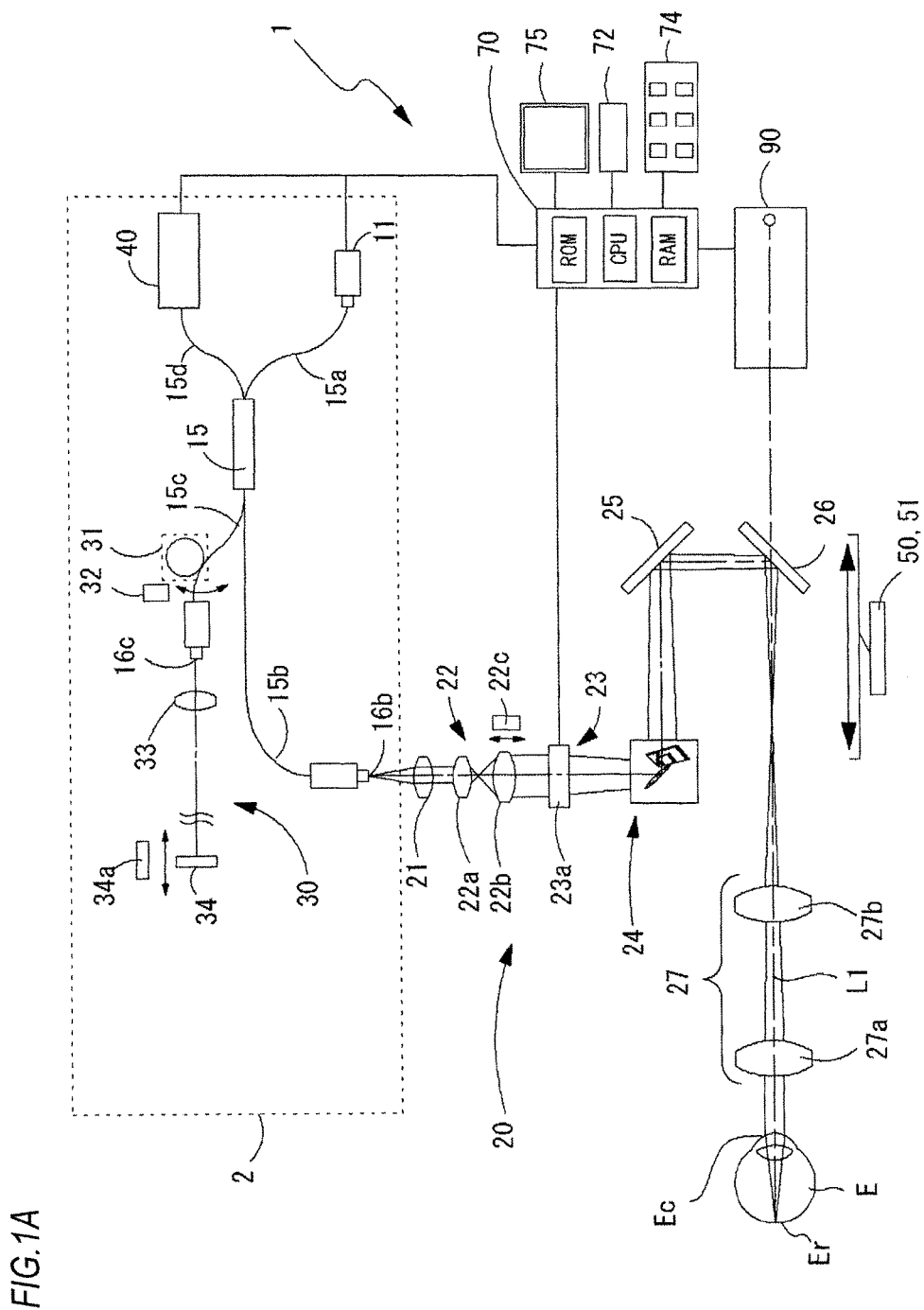
FIG. 1A is a schematic diagram illustrating a configuration of an ophthalmic imaging device according to a first embodiment, and illustrates an optical arrangement during capture of an image of a fundus.
Figure 1B:
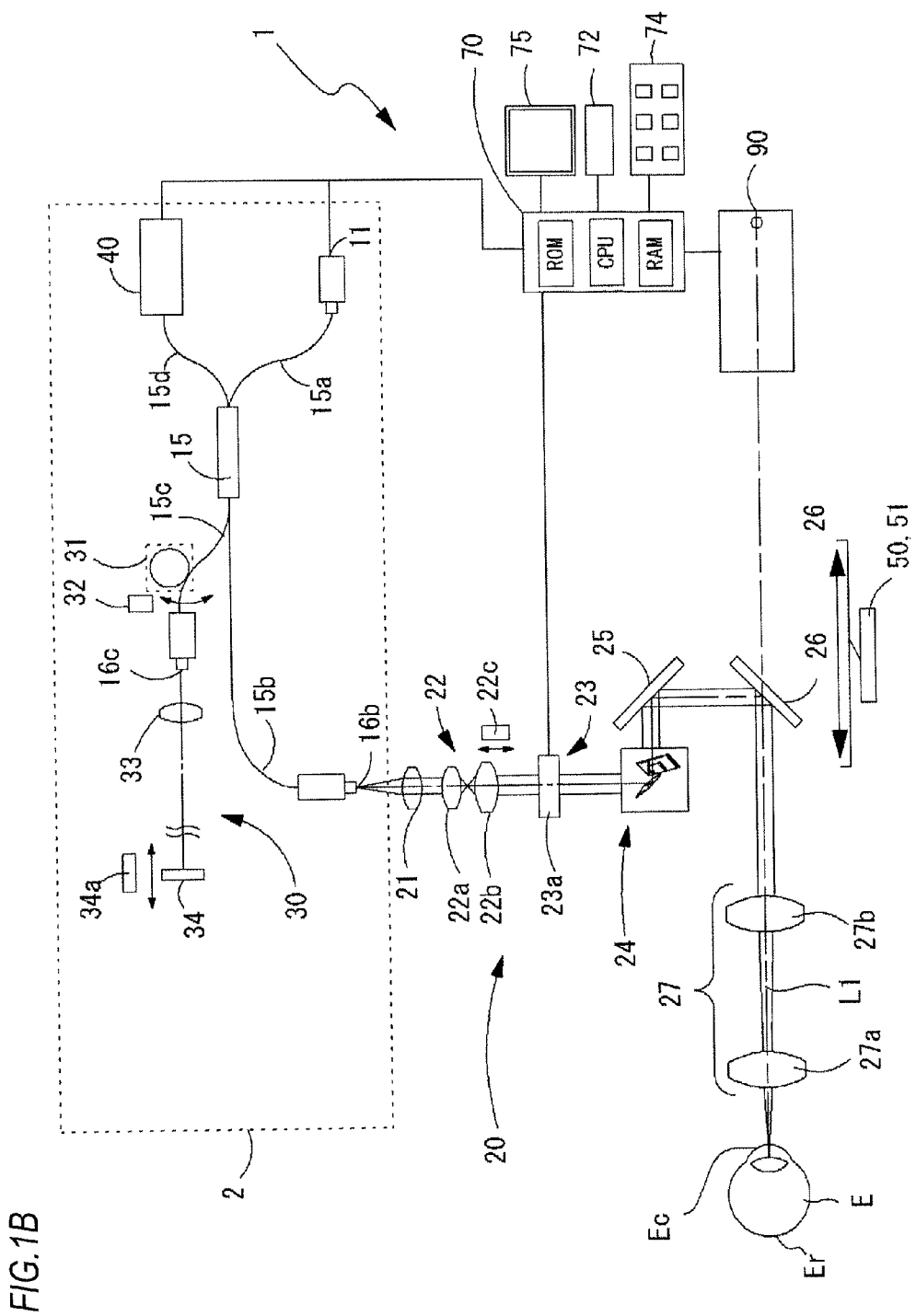
FIG. 1B is a schematic diagram illustrating a configuration of the ophthalmic imaging device according to the first embodiment, and illustrates an optical arrangement during capture of an image of an anterior ocular segment.

The OCT device 1 illustrated in FIGS. 1A and 1B mainly includes an interference optical system 2 (OCT optical system), a measurement optical system (light guide optical system) 20, and a control unit 70. In the first embodiment, the OCT device 1 further includes a fixation target projection unit 90 (second optical system), a storage unit (memory) 72, an operation unit 74, and a monitor 75.

First, the interference optical system 2 will be described. The interference optical system 2 splits luminous flux emitted from a light source 11 into measurement light and reference light. The interference optical system 2 guides measurement light to the eye E and guides reference light to a reference optical system 30. In addition, the interference optical system 2 detects interference of the measurement light and reference light with which the eye E is irradiated, by a detector (photodetector) 40. More specifically, in the present embodiment, an interference signal of light generated by a combination of measurement light reflected (or backscattered) from the eye E and reference light is detected by the detector 40.

In a case of SD-OCT, a low coherent light source (broadband light source) is used as the light source 11, and the detector 40 is provided with a spectral optical system (spectral meter) that spectrally splits interference light into frequency components. The spectral meter is constituted by, for example, a diffraction grating and a line sensor.

In addition, in a case of SS-OCT, a wavelength swept light source (wavelength variable light source) which temporally changes an emission wavelength at a high speed is used as the light source 11, and the detector 40 is provided with, for example, a single light receiving element. The light source 11 is constituted by, for example, a light source, a fiber ring resonator, and a wavelength selection filter. In addition, examples of the wavelength selection filter include a combination of a diffraction grating and a polygon mirror, and a wavelength selection filter using a Fabry-Perot etalon.

In OCT device 1, the optical arrangement of the measurement optical system 20 is switched. As an example, switching to an optical arrangement illustrated in FIG. 1A and an optical arrangement illustrated in FIG. 1B may be performed. In the optical arrangements illustrated in FIGS. 1A and 1B, depth bands of portions in which a tomographic image is captured by the OCT device 1 are different from each other. Hereinafter, the first embodiment will be described focusing on a specific example in which SD-OCT is applied to the OCT device 1 having the optical arrangements illustrated in FIGS. 1A and 1B.

The interference optical system 2 illustrated in FIGS. 1A and 1B includes a light source 11, optical fibers 15a, 15b, 15c, and 15d, a splitter 15, a reference optical system 30, and a detector 40.

The light source 11 emits low coherent light beams which are used as measurement light and reference light of the interference optical system 2. For example, an SLD light source or the like may be used as the light source 11. As a specific example in this case, the light source 11 may emit light having a center wavelength in a range of λ=800 nm to 1100 nm. Light from the light source 11 is guided to the splitter 15 through the optical fiber 15a.

Meanwhile, the optical fibers 15a, 15b, 15c, and 15d allow light to pass therethrough to thereby connect the splitter 15, the light source 11, the measurement optical system 20, the reference optical system 30, the detector 40, and the like to each other.

The splitter 15 splits light guided from the light source 11 (through the optical fiber 15a) into measurement light and reference light. The measurement light is guided to the measurement optical system 20 through the fiber 15b. On the other hand, the reference light is guided to the reference optical system 30 through the fiber 15c and a polarizer 31.

In the examples illustrated in FIGS. 1A and 1B, the splitter 15 also serves as a combination unit (combiner) which couples light guide paths of return light of measurement light guided to the eye E and reference light to each other (to be described later in detail). The splitter 15 may be, for example, a fiber coupler. Hereinafter, the splitter 15 will be referred to as a coupler 15.

For convenience, the measurement optical system 20 will be described here. The measurement optical system 20 guides, for example, measurement light to the eye E. As an example, the measurement optical system 20 illustrated in FIGS. 1A and 1B includes a collimator lens 21, a luminous flux diameter adjustment unit (adjuster) 22, a condensing position variable optical system (condensing position variable lens system) 23, a scanning unit (optical scanner) 24, a mirror 25, a dichroic mirror 26, and an objective optical system 27.

The collimator lens 21 collimates measurement light emitted from an end 16b of the optical fiber 15b.

The luminous flux diameter adjustment unit 22 is disposed in a light path between the interference optical system 2 and the scanning unit 24 (in other words, an optical scanner), and is used to change the luminous flux diameter of measurement light in the light path. In the examples illustrated in FIGS. 1A and 1B, the luminous flux diameter adjustment unit 22 is provided in a light path between the coupler 15 and the scanning unit 24 in the measurement optical system 20. The luminous flux diameter adjustment unit 22 may be, for example, at least any one of an aperture capable of being inserted into and removed from a light path by an inserting and removing mechanism, a variable beam expander, and a variable aperture capable of adjusting the diameter of an opening. As a specific example, the luminous flux diameter adjustment unit 22 illustrated in FIGS. 1A and 1B is a variable beam expander. As illustrated in FIGS. 1A and 1B, the variable beam expander may include, for example, two lenses 22a and 22b and a driving unit 22c. The driving unit 22c changes a positional relationship between the lenses 22a and 22b in a direction of an optical axis based on a control signal from the control unit 70. Thereby, the luminous flux diameter (and NA) of measurement light is changed.

The condensing position variable optical system 23 is used to change the condensing position of measurement light in a direction of an optical axis L1. The condensing position variable optical system 23 includes at least one lens 23a, and adjusts the condensing position of measurement light in the direction of the optical axis L1 using the lens 23a. In the examples illustrated in FIGS. 1A and 1B, the condensing position variable optical system 23 is provided in a light path between the coupler 15 and the scanning unit 24. Meanwhile, in the present embodiment, the condensing position variable optical system 23 is disposed between the luminous flux diameter adjustment unit 22 and the scanning unit 24. However, the arrangements of the luminous flux diameter adjustment unit 22 and condensing position variable optical system 23 are not necessarily limited thereto. For example, the arrangements may be replaced with each other. In addition, a relay optical system and the like may be interposed therebetween. The lens 23a constitutes a focus optical system that determines the condensing position of measurement light in the direction of the optical axis L1. The focus optical system may be constituted by only the lens 23a, or may be constituted by the lens 23a and other optical elements. The condensing position variable optical system 23 may be realized by, for example, a configuration in which either a refractive power of the lens 23a or a positional relationship between the objective optical system 27 and the lens 23a with respect to the direction of the optical axis L1 is adjusted. Meanwhile, the adjustment of the positional relationship between the objective optical system 27 and the lens 23a may be realized by, for example, any of the position of the lens 23a with respect to the direction of the optical axis L1, the length of a light path between the lens 23a and the objective optical system 27a, and the insertion or removal of a lens into or from a measurement light path. In this case, a driving unit (actuator) moving the lens 23a in a desired direction is controlled by the control unit 70. In the first embodiment, the condensing position variable optical system 23 may also be used as a diopter correction optical system that corrects diopter in a case where an image of the inside of an eye such as a fundus Er is captured (to be described later).

In the examples illustrated in FIGS. 1A and 1B, the lens 23a is a variable focus lens. The lens 23a can changes a focal position in a state of standing still with respect to the optical axis L1. The lens 23a changes a refractive power in accordance with a magnitude of an applied voltage which is set by the control unit 70. A liquid crystal lens or the like is known as a typical variable focus lens. Meanwhile, the refractive power variable lens is not limited to a liquid crystal lens, and may be, for example, a liquid lens, a nonlinear optical member, a molecular member, a rotationally asymmetric optical member, or the like.

Figure 2:
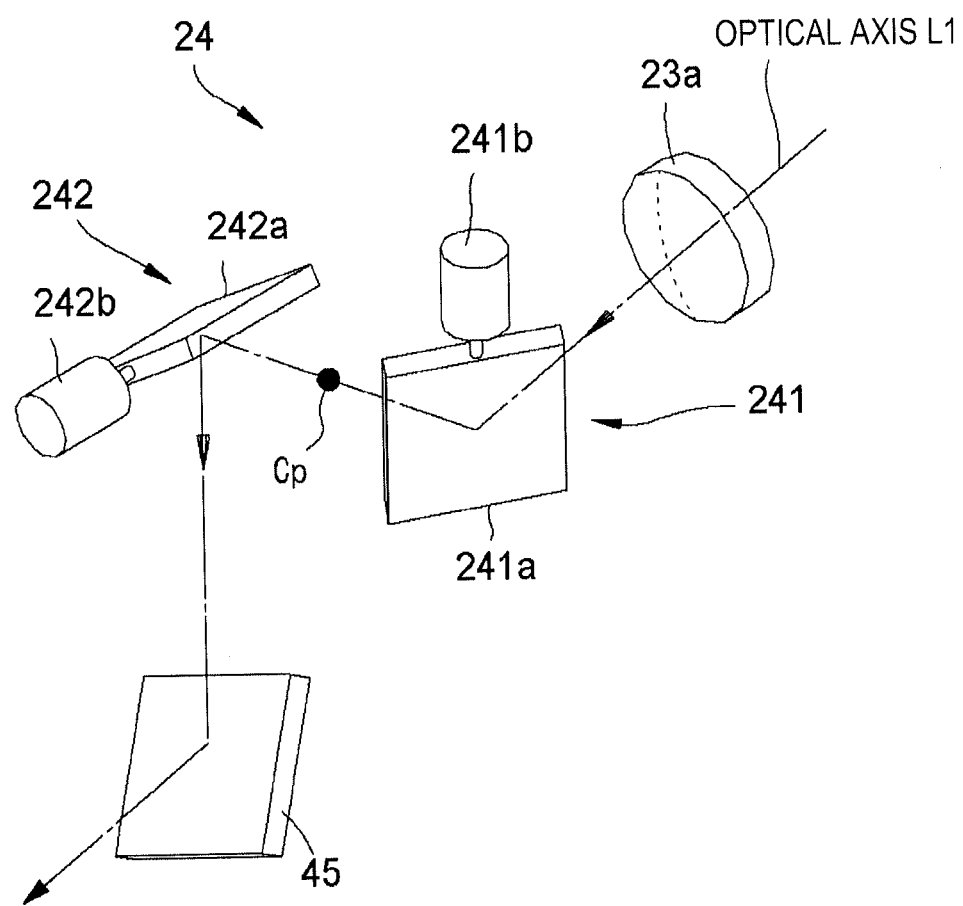
FIG. 2 is an enlarged view illustrating an example of a scanning unit.

The scanning unit 24 includes an optical scanner that deflects measurement light from the OCT optical system in order to scan the measurement light. The scanning unit 24 may include, for example, two galvano mirrors 241 and 242 (examples of an optical scanner). In the example of FIG. 2, reference numeral 241 denotes an X scanning galvano mirror, and reference numeral 242 denotes a Y scanning galvano mirror. Each of the galvano mirrors 241 and 242 may include mirror units 241a and 242a and driving units 241b and 242b (for example, motors) which rotate the respective mirror units 241a and 242a. The control unit 70 independently controls the orientation of each of the galvano mirrors 241 and 242 to thereby change a traveling direction of measurement light. As a result, it is possible to scan the eye E with measurement light in vertical and horizontal directions. Meanwhile, the scanning unit 24 can use an optical scanner other than the galvano mirrors 241b and 242b. For example, a reflective scanner (for example, a MEMS scanner, a resonant scanner, a polygon mirror, or the like may be used) may be used, or an acoustic optical element or the like may be used.

In the examples illustrated in FIGS. 1A and 1B, measurement light of which the traveling direction is changed by the scanning unit 24 is reflected from each of the mirror 25 and the dichroic mirror 26 that are configured such that the respective mirror surfaces thereof are disposed with a right angle therebetween. Thereby, the measurement light is turned back in a direction opposite to a direction during the emission thereof from the scanning unit 24. As a result, the measurement light is guided to the objective optical system 27.

In the embodiment, the objective optical system 27 is fixedly arranged. Specifically, the objective optical system 27 is disposed between the scanning unit 24 and the eye E in the measurement optical system 20. The objective optical system 27 guides measurement light deflected by an optical scanner (the galvano mirrors 241 and 242 in the present embodiment) to the eye E. In the present embodiment, the objective optical system 27 is formed as a lens system (objective optical system) having a positive power. For this reason, measurement light from the scanning unit 24 passes through the objective optical system 27 to be bent to the optical axis L1 side. Meanwhile, in FIGS. 1A and 1B, the objective optical system 27 is illustrated as an optical system constituted by two lenses 27a and 27b for convenience, but the number of lenses constituting the objective optical system 27 is not limited thereto. The objective optical system 27 may be replaced with one lens, or may be replaced with three or more lenses (see, for example, FIG. 4). In addition, the objective optical system 27 is not limited to a lens system, and may be, for example, a mirror system, may be an optical system constituted by a combination of a lens and a mirror, or may be an optical system including an optical member other than a lens and a mirror.

In the measurement optical system 20, when measurement light is emitted from the end 16b of the optical fiber 15b, the measurement light is collimated by the collimator lens 21. Thereafter, the measurement light passes through the luminous flux diameter adjustment unit 22 and the condensing position variable optical system 23 and reaches the scanning unit 24. The measurement light is reflected from two galvano mirrors provided in the scanning unit 24 and is then reflected from the mirror 25 and the dichroic mirror 26. As a result, the measurement light is incident on the objective optical system 27. In addition, the measurement light passes through the objective optical system 27 and is guided to the eye E. Thereafter, the measurement light is reflected and scattered from the eye E, and is consequently incident on the end 16b of the optical fiber 15b by following the measurement optical system 20 in a reverse direction. The measurement light which is incident on the end 16b is incident on the coupler 15 through the optical fiber 15b.

The OCT device 1 includes a driving unit (actuator). The driving unit displaces the relative position of the measurement optical system 20 with respect to the direction of the optical axis L1 which is the relative position of the scanning unit 24 (in other words, the galvano mirrors 241 and 242 which are optical scanners) with respect to the objective optical system 27. In more detail, the relative position of the scanning unit 24 with respect to the rear side focal position (or the conjugate position thereof) of the objective optical system 27 is changed by the driving of the driving unit. The turning position of measurement light is changed in the direction of the optical axis L1 due to the displacement of the relative position (to be described later in detail). The driving unit may change a relative distance between the scanning unit 24 and the objective optical system 27 by moving at least one of the scanning unit 24 and an optical element disposed between the objective optical system 27 and the scanning unit 24. In the example of FIGS. 1A and 1B, the OCT device 1 includes the driving unit 50. In the examples illustrated in FIGS. 1A and 1B, an interval (length of a light path) between the objective optical system 27 and the scanning unit 24 is changed by the driving of the driving unit 50, and accordingly, the relative position of the scanning unit 24 with respect to the objective optical system 27 is displaced. The relative position is changed in response to a depth band of the eye E of which the tomographic image is captured.

In the examples illustrated in FIGS. 1A and 1B, the driving unit 50 integrally moves two mirrors (the mirror 25 and adichroic mirror), which are configured such that the respective mirror surfaces thereof are disposed with a right angle therebetween, in a predetermined direction. In the present embodiment, the two mirrors are moved in a direction of an optical axis of the objective optical system 27. As a result, the length of a light path between the scanning unit 24 and the objective optical system 27 is changed (for example, FIG. 1A→FIG. 1B and FIG. 1B→FIG. 1A). For example, in a case where a depth band having a tomographic image obtained therein is switched between an anterior ocular segment and a fundus Er, it is necessary to change the length of a light path between the scanning unit 24 and the objective optical system 27 to a relatively large length. On the other hand, in the example of FIG. 1A, measurement light emitted from the scanning unit 24 is turned back by two mirrors. For this reason, in a case where the two mirrors are moved, it is possible to set a change in the length of the light path between the scanning unit 24 and the objective optical system 27 (in other words, the amount of displacement of the scanning unit 24 with respect to the objective optical system 27 in the direction of the optical axis L1) to be twice the amount of movement of the two mirrors 25 and 26. Therefore, it is possible to suppress a space required to displace the position of the scanning unit 24 with respect to the objective optical system 27 in the direction of the optical axis L1 of the measurement optical system 20.

In addition, as illustrated in FIGS. 1A and 1B, the OCT device 1 may include a sensor 51 for detecting the position of the scanning unit 24 with respect to the objective optical system 27. Various devices can be used as the sensor 51. For example, a linear displacement sensor such as a potentiometer may be used as the sensor 51.

Here, returning to a description of the interference optical system 2, the reference optical system 30 generates reference light. The reference light is light combined with reflected light of measurement light which is reflected by the fundus Er. The reference optical system 30 may be a Michelson type or may be a Mach-Zehnder type. The reference optical system 30 illustrated in FIGS. 1A and 1B is constituted by a reflection optical system (for example, a reference mirror 34). In the examples of FIGS. 1A and 1B, light from the coupler 15 is reflected by the reflection optical system to be returned to the coupler 15 again, and consequently is guided to the detector 40. However, the present disclosure is not necessarily limited thereto, and the reference optical system 30 may be constituted by a transmission optical system (for example, an optical fiber). In this case, the reference optical system 30 transmits reference light which is split by the coupler 15 without returning the reference light to the coupler 15 to thereby guide the reference light to the detector 40.

In the examples illustrated in FIGS. 1A and 1B, the reference optical system 30 includes an optical fiber 15c, an end 16c of the optical fiber 15c, a collimator lens 33, and a reference mirror 34 in a light path between the splitter 15 to the reference mirror 34. The optical fiber 15c changes a polarization direction of reference light, and is thus rotated and moved by a driving unit 32. That is, the optical fiber 15c and the driving unit 32 are used as the polarizer 31 for adjusting a polarization direction. Meanwhile, the polarizer is not limited to having the above-mentioned configuration, and polarization states of measurement light and reference light may be made substantially consistent with each other by driving a polarizer which is disposed in a light path of the measurement light or a light path of the reference light. For example, a polarizer that changes a polarization state by using a ½ wavelength plate or a ¼ wavelength plate or applying pressure to a fiber to thereby deform the fiber, or the like can be used.

Meanwhile, the polarizer 31 (polarization controller) may be configured to adjust a polarization direction of at least any one of measurement light and reference light in order to make polarization directions of the measurement light and the reference light consistent with each other. For example, the polarizer 31 may be configured to be disposed in a light path of measurement light.

In addition, the reference mirror 34 is displaced by a reference mirror driving unit 34a in a direction of an optical axis L2. The length of a light path of reference light is adjusted by the displacement of the reference mirror 34.

Reference light emitted from the end 16c of the optical fiber 15c changes to parallel luminous flux by the collimator lens 21, and is reflected by the reference mirror 34. Thereafter, the reference light is condensed by the collimator lens 21 and is incident on the end 16c of the optical fiber 15c. The reference light which is incident on the end 16c reaches the coupler 15 through the optical fiber 15c and the optical fiber 31 (polarizer 31).

In the examples of FIGS. 1A and 1B, reference light reflected by the reference mirror 34 and return light (in other words, measurement light reflected or scattered by the eye E) of measurement light condensed on the eye E are combined with each other by the coupler 15 to change to interference light. The interference light is emitted from the end 16b through the fiber 15b. As a result, the interference light is guided to the detector 40.

The detector (here, a spectrometer unit) 40 splits interference light of reference light and measurement light for each frequency (wavelength) in order to obtain an interference signal for each frequency (wavelength), and receives the split interference light.

The detector 40 illustrated in FIGS. 1A and 1B may include optical systems (none of which is not shown in the drawing) such as a collimator lens, a grating mirror (diffraction grating), and a condensing lens. For example, a one-dimensional light receiving element (line sensor) may be applied to the body (light receiving element portion) of the detector 40. The detector 40 has sensitivity with respect to a wavelength of light emitted from the light source 11. As described above, in a case where light in an infrared region is emitted from the light source 11, the detector 40 having sensitivity in an infrared region may be used.

The interference light emitted from the end 16b changes to parallel light by the collimator lens 21, and is then split into frequency components by the grating mirror 42. In addition, the interference light which is split into frequency components is condensed on a light receiving surface of the detector 40 through a condensing lens 43. Thereby, spectrum information (spectrum signal) of an interference fringe on the detector 40 is obtained. The spectrum information is input to the control unit 70, and is analyzed using Fourier transform in the control unit 70. In addition, as an analysis result, a tomographic image (see FIG. 3) of an eye is formed. In addition, as an analysis result, information in the depth direction of the eye E can be measured.

Here, the control unit 70 can perform scanning with measurement light by the scanning unit 24 in a transverse direction of the eye E to thereby acquire a tomographic image. For example, it is possible to acquire a tomographic image of the fundus Er of the eye in an XZ plane or a YZ plane by performing scanning in an X direction or a Y direction (Meanwhile, in the first embodiment, such a method of obtaining a tomographic image by one-dimensionally scanning the fundus Er with measurement light is referred to as B scanning). Meanwhile, the acquired tomographic image is stored in the storage unit 72 connected to the control unit 70. Furthermore, scanning with measurement light can be two-dimensionally performed in an XY direction by controlling the driving of the scanning unit 24 to thereby form a two-dimensional moving image of the fundus Er of the subject's eye in the XY direction and a three-dimensional image of the fundus Er of the eye based on an output signal from the detector 40.

Next, the fixation target projection unit 90 will be described. The fixation target projection unit 90 includes an optical system for guiding a gaze direction of the eye E. The fixation target projection unit 90 includes a fixation target (fixed light source 91) which is presented in the eye E. The fixation target projection unit 90 may be configured to guide the eye E in a plurality of directions. Here, the dichroic mirror 26 has characteristics of transmitting light having a wavelength component used as measurement light of the interference optical system 2 and transmitting light having a wavelength component used for the fixation target projection unit 90. Therefore, fixation target luminous flux emitted from the fixation target projection unit 90 is applied to the fundus Er of the eye E through the objective optical system 27. Thereby, the subject's visual fixation can be performed.

Control System

Next, a control system of the OCT device 1 will be described. The control unit (controller) 70 controls each unit of the OCT device 1. For example, the control unit 70 may be configured to include a CPU (processor), a memory, and the like. In addition, in the first embodiment, the control unit 70 processes, for example, an output signal (in other words, an interference signal) from the detector 40 to thereby acquire depth information of the eye E. The depth information may be at least any one of image information of a tomographic image or the like, dimension information indicating a dimension of each portion of the eye E, information indicating the amount of movement in a portion to be irradiated with measurement light, and an analysis signal (of a complex number) including information of a polarization characteristic. In the first embodiment, the control unit 70 also serves as an image processor that forms a tomographic image of the eye E based on an interference signal. In addition, the control unit 70 of the first embodiment performs various image processing other than the formation of a tomographic image. The image processing may be performed by a dedicated electronic circuit (for example, an image processing IC not shown in the drawing) which is provided in the control unit 70, or may be performed by a processor (for example, a CPU).

A storage unit 72, an operation unit (user interface) 74, and a monitor 75 are connected to the control unit 70. The storage unit 72 may include a rewritable non-fugitive storage medium, or may be, for example, any of a flash memory, a hard disk, and the like. An image and measurement data obtained as a result of image capturing and measurement are stored in the storage unit 72. A program and fixed data that specify an image capturing sequence in the OCT device 1 may be stored in the storage unit 72, or may be stored in a ROM within the control unit 70. In addition to the light source 11, the detector 40, and various driving units 22c, 23a, 241a, 242b, 32, 34a, and 50, the sensor 51 and the like are connected.

Operation of Switching Image Capturing Depth Band

Next, an operation of switching an image capturing depth band in the OCT device 1 configured as described above will be described with reference to FIGS. 4A and 4B. In the first embodiment, the control unit 70 controls the driving unit 50 in order to switch an image capturing depth band, and displaces a turning position of measurement light in an eye E in the direction of the optical axis L1. The turning position is displaced in accordance with the relative position of the scanning unit 24 with respect to the objective optical system 27. in other words, in the first embodiment, the control unit 70 changes the relative position of the scanning unit 24 with respect to the objective optical system 27 by the driving unit 50, and consequently adjusts the turning position of measurement light in the eye E in the direction of the optical axis L1. At this time, the control unit 70 changes the turning position of the measurement light at least between a first position and a second position. The first position corresponds to a first depth band of the eye E, and the second position corresponds to a second depth band of the eye E which is different from the first depth band. In addition, the second position is different from the first position in a direction of the optical axis of the measurement optical system (depth direction of the eye E).

Figure 4A:
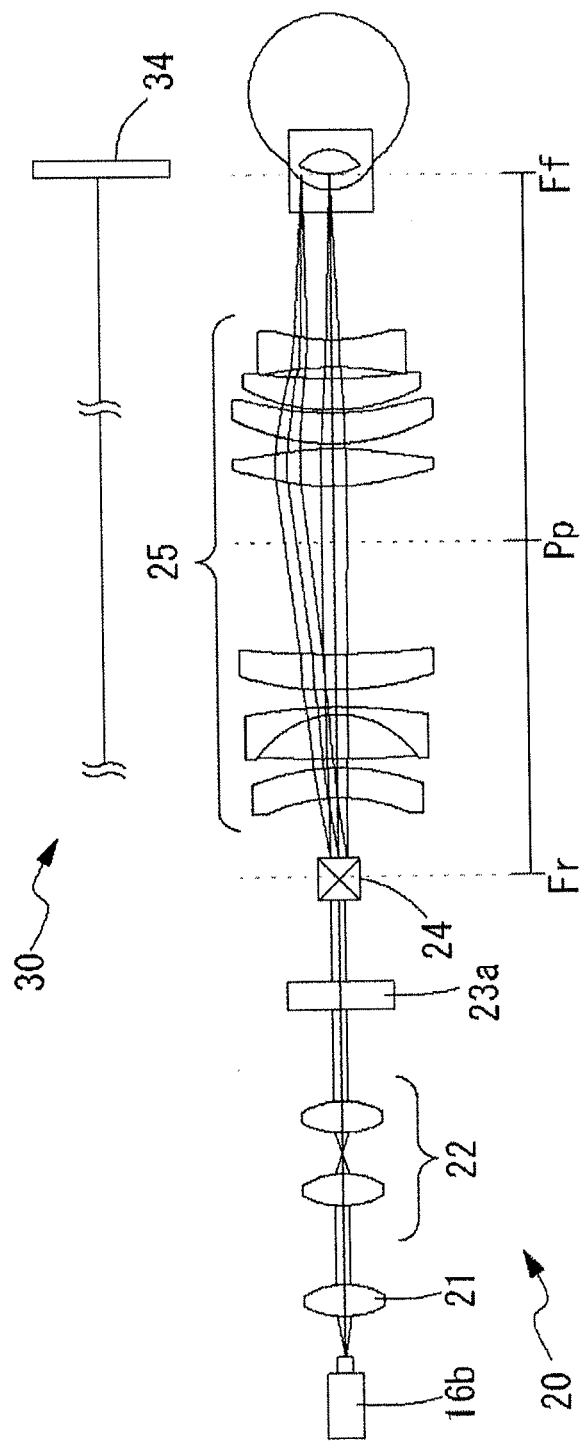
FIG. 4A is a diagram illustrating a positional relationship between units of an interference optical system during capture of an image of an anterior ocular segment.
Figure 4B:
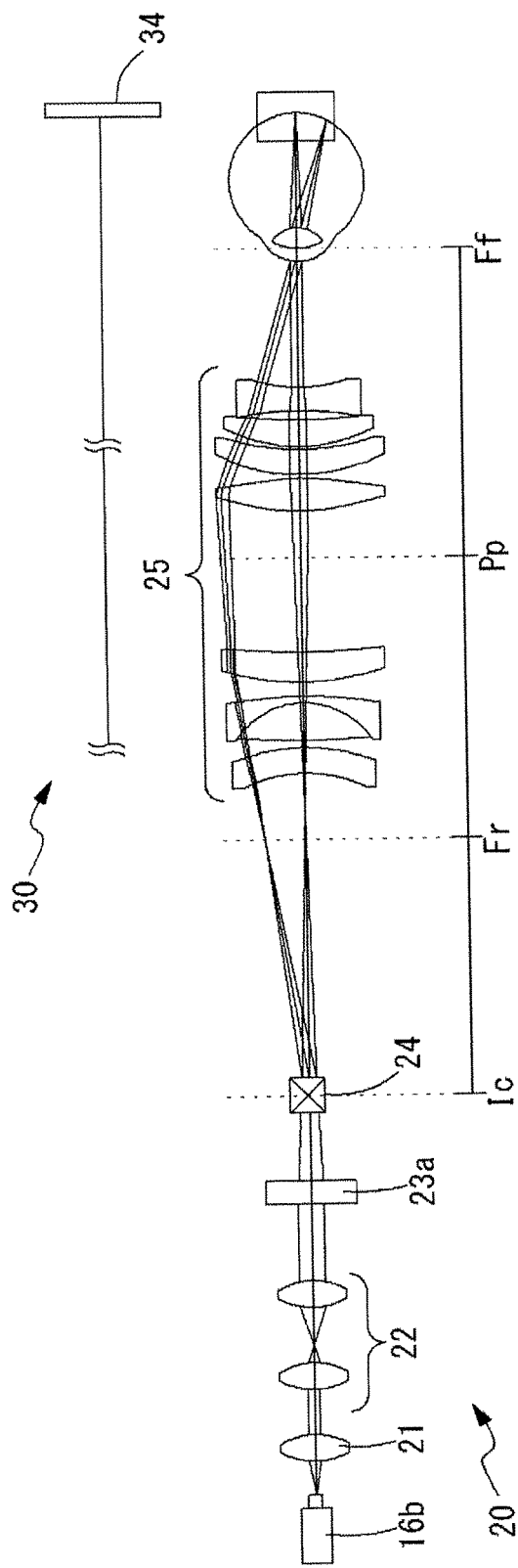
FIG. 4B is a diagram illustrating a positional relationship between units of the interference optical system during capture of an image of a fundus.

In addition, the first position and the second position may be turning positions that differ in the number of Fourier transformed images (or the number of pupil images) of a pupil which are formed in a section between the scanning unit 24 and an end on a subject side in the objective optical system 27. In FIGS. 4A and 4B, the end on the subject side in the objective optical system 27 is a lens surface which is disposed closest to the eye E in the objective optical system 27. Meanwhile, in a case where the objective optical system 27 is a mirror system, a mirror surface disposed closest to the eye E is an end on a subject side. Switching is performed between even and odd numbers of Fourier transformed images (or the number of pupil images) of a pupil in the above-mentioned section (to be described later in detail) by the switching of the turning position between the first position and the second position. Meanwhile, at this time, switching between even and odd numbers may be performed in both the number of Fourier transformed images of a pupil and the number of pupil images, or may be performed in either of them. Switching between even and odd numbers of Fourier transformed images (or the number of pupil images) of a pupil in the above-mentioned section is performed at the first position and the second position, and thus, for example, a tomographic image of an anterior ocular segment tends to be satisfactorily captured at either the first position or the second position, and a tomographic image of a fundus Er tends to be satisfactorily captured at the other position. Meanwhile, the Fourier transformed image of the pupil is formed at a position where parallel luminous flux emitted from the pupil is condensed (for example, the position of Fr in FIG. 4B).

Here, FIG. 4A illustrates a positional relationship between units of the measurement optical system 20 during capture of an image of an anterior ocular segment (first depth band in the first embodiment). FIG. 4B illustrates a positional relationship between units of the measurement optical system 20 during capture of an image of a fundus Er (second depth band in the first embodiment). Meanwhile, in FIGS. 4A and 4B, the mirror 25 and the dichroic mirror 26 are not shown. Meanwhile, in FIGS. 4A and 4B, Ff denotes a front side focus of the objective optical system 27, and Fr denotes a rear side focus of the objective optical system 27. In addition, Ic denotes a position conjugate to the pupil of the eye E with respect to the objective optical system 27.

In the examples of FIGS. 4A and 4B, the control unit 70 controls the driving unit 50 during capture of an image of an anterior ocular segment and during capture of an image of a fundus Er to thereby switch a turning position of measurement light in the direction of the optical axis L1. At this time, the control unit 70 may adjust the length of a light path in the reference optical system 30 in association with changes in relative positions of the objective optical system 27 and the scanning unit 24. In addition, at this time, the control unit 70 may control the condensing position variable optical system 23 to thereby switch a condensing position of measurement light. Furthermore, the control unit 70 may control the luminous flux diameter adjustment unit 22 to thereby adjust NA. Such a change in the position of the scanning unit 24 (in other words, a change in an image capturing depth band) may be performed based on, for example, a switching signal which is output to the control unit 70 from the operation unit 74. In addition, the control unit 70 may automatically perform switching in a series of image capturing sequences. Hereinafter, a detailed description will be given.

Image Capturing of Anterior Ocular Segment

As illustrated in FIG. 4A, the control unit 70 brings the scanning unit 24 closer to the objective optical system 27 during capture of an image of an anterior ocular segment than during capture of an image of a fundus (see FIG. 4B). As a result, a turning position of measurement light is set to a position in which the number of Fourier transformed images of a pupil is set to an even number. In the example of FIG. 4A, the number of Fourier transformed images of a pupil is "0". In this case, the control unit 70 may dispose the scanning unit 24 at a rear side focal position Fr of the objective optical system 27. For example, the control unit 70 positions the scanning unit 24 at the rear side focal position Fr based on a detected signal of the sensor 51. It is desired that an optical scanner (galvano mirrors 241 and 242 in the first embodiment) constituting the scanning unit 24 is disposed in the vicinity of the rear side focal position Fr in an allowable range of measurement accuracy (or image quality of a tomographic image) during the positioning. For example, the control unit 70 may position an intermediate point Cp (see FIG. 2) between two optical scanners (galvano mirrors 241 and 242 in the first embodiment) at the rear side focal position Fr, or may position a reflection surface of any one optical scanner at the rear side focal position Fr. Naturally, other arrangements may be made.

As a result of the arrangement of the scanning unit 24 at the rear side focal position Fr of the objective optical system 27, a main light beam of measurement light becomes telecentric (or substantially telecentric) on an object side (side of an eye) of the objective optical system 27. In other words, in the first embodiment, an optical system (for convenience, referred to as a scanning optical system) which is constituted by the scanning unit 24 and the objective optical system 27 is formed as an object-side telecentric optical system. In this case, a turning position (first position in the first embodiment) of measurement light in the eye E can be considered to be an infinite point on the optical axis L1. In addition, in this case, a main light beam of measurement light with which a pupil surface of the eye E is irradiated from the front surface of the objective optical system 27 (in other words, a lens surface disposed closest to the eye) becomes parallel (substantially parallel) to the optical axis L1 regardless of the direction of the measurement light reflected by the scanning unit 24. Thereby, it is possible to reduce a change in the magnification of a captured image due to a change in the position of the eye E. As a result, it is possible to measure a distance from a captured tomographic image of an anterior ocular segment with a high level of accuracy. In addition, irradiation with telecentric measurement light is performed during capture of an image of an anterior ocular segment, and thus distortion of the tomographic image due to a positional deviation of the eye E in a working distance direction is not likely to occur. Thereby, an examiner can observe a tomographic image with little distortion and easily performs diagnosis by the tomographic image. Furthermore, the recovery efficiency of return light (reflected light or back scattered light) from a portion to be measured is improved by irradiation with telecentric measurement light during capture of the image of the anterior ocular segment, and thus it is possible to reduce the darkening of a peripheral portion of the image.

Meanwhile, in the example of FIG. 4A, a description is given of a case where the scanning unit 24 is disposed at the rear side focal position Fr of the objective optical system 27 under the control of the driving unit 50 in order to perform irradiation with telecentric measurement light, but the driving unit 50 may be controlled so that the scanning unit 24 is disposed at a position conjugate to the rear side focal position Fr through a lens system and the like. Meanwhile, in the present disclosure, the term "conjugate" as used herein is not necessarily limited to an optically complete conjugate relationship. In the present disclosure, the "conjugate" relationship may not only be a complete positional relationship but also be a positional relationship deviating from a complete conjugate relationship in an allowable range of measurement accuracy (or image quality of a tomographic image).

In addition, in the first embodiment, the control unit 70 sets the length of a light path of the reference optical system 30 during capture of an image of an anterior ocular segment to be smaller than that during capture of an image of a fundus in accordance with the length of a light path of measurement light between the anterior ocular segment and a fundus Er. In more detail, the length of the light path of the reference optical system 30 is adjusted so that the length of a light path of return light of measurement light from the anterior ocular segment becomes equal to the length of the light path of the reference optical system 30. Thereby, an interference signal generated by satisfactory interference of return light of measurement light and reference light is satisfactorily obtained by the detector 40. The control unit 70 forms an image based on the interference signal, thereby obtaining a tomographic image W2 which is an image of the anterior ocular segment (see FIG. 3).

In addition, as illustrated in FIG. 4A, the control unit 70 controls the condensing position variable optical system 23 during capture of an image of an anterior ocular segment to thereby set a condensing position of measurement light in the anterior ocular segment. In this case, the control unit 70 may control the condensing position variable optical system 23 so that measurement light which is incident on the scanning unit 24 from the lens 23a is slightly diffused. As a specific example, the control unit 70 may set a refractive power of a variable focus lens (lens 23a) to a negative value. Thereby, it is preferable that the condensing position is set to be an intermediate position (more preferably, an intermediate position between the front surface and rear surface of the lens of an eye) between the front surface of the cornea of the eye and the rear surface of the lens of the eye. In this case, a region having a relatively high resolution in a tomographic image becomes wider than that in a case where a condensing position is set on a cornea surface.

In addition, as illustrated in FIG. 4A, the control unit 70 controls the luminous flux diameter adjustment unit 22 during capture of an image of an anterior ocular segment to thereby makes the luminous flux diameter of measurement light in a light path between the interference optical system 2 and the scanning unit 24 (in other words, an optical scanner) smaller than that during capture of an image of a fundus. Thereby, NA of luminous flux which is incident on the eye E becomes small. In other words, the depth of focus with respect to the objective optical system 27 becomes larger than that during capture of an image of a fundus. As a result, a range in which an interference signal from the detector 40 is satisfactorily obtained in the depth direction o the eye E is widened. Accordingly, there is a tendency for an image of the anterior ocular segment to be captured by the optical coherence tomography 1 over a wide range (for example, a range from the front surface of the cornea to the rear surface of the lens of the eye).

Capture of Image of Fundus

On the other hand, as illustrated in FIG. 4B, the control unit 70 keeps the scanning unit 24 farther away from the objective optical system 27 during capture of an image of a fundus than that during capture of an image of an anterior ocular segment (see FIG. 4A). As a result, a turning position of measurement light is set to a position in which the number of Fourier transformed images of a pupil is set to an odd number. In the example of FIG. 4B, the number of Fourier transformed images of a pupil is "1". In this case, the control unit 70 may dispose the scanning unit 24 at a position Ic conjugate to the pupil of an eye E, with respect to the objective optical system 27. For example, the control unit 70 positions the scanning unit 24 at the pupil conjugate position Ic based on a detected signal of the sensor 51. For example, the scanning unit 24 may be disposed so that the intermediate point Cp (see FIG. 2) between two optical scanners (galvano mirrors in the first embodiment) which constitute the scanning unit 24 is conjugate to the pupil with respect to the objective optical system 27. Naturally, other arrangements may be made. The scanning unit 24 is disposed at the pupil conjugate position Ic, and thus measurement light emitted from the front surface (lens surface on a side closest to the eye) of the objective optical system 27 turns centering on the position of the pupil (turning point) in association with the driving of the scanning unit 24. In other words, in this case, a turning position (second position in the first embodiment) of measurement light in the eye E is set to be the position of the pupil. Thereby, it is possible to irradiate the fundus Er with measurement light while suppressing vignetting of the measurement light. As a result, it is possible to capture a tomographic image of the fundus Er over a wide range of the fundus Er. Meanwhile, in the present embodiment, a case where the scanning unit 24 is disposed at the pupil conjugate position Ic during capture of an image of a fundus is described, but the position of the scanning unit may be a position which is substantially conjugate to a predetermined area of an anterior ocular segment, and may be a position which is conjugate to, for example, the cornea of the eye.

In addition, in the first embodiment, the control unit 70 sets the length of a light path of the reference optical system 30 during capture of an image of a fundus to be larger than that during capture of an image of an anterior ocular segment in accordance with the length of a light path of measurement light between the anterior ocular segment and the fundus Er. In more detail, the length of the light path of the reference optical system 30 is adjusted so that the length of a light path of return light of measurement light from the fundus Er becomes equal to the length of the light path of the reference optical system 30. Thereby, an interference signal generated by satisfactory interference of return light of measurement light from the fundus Er and reference light is satisfactorily obtained by the detector 40. The control unit 70 forms an image based on the interference signal, thereby obtaining a tomographic image W1 which is an image of the fundus (see FIG. 3).

As illustrated in FIG. 4B, the control unit 70 controls the condensing position variable optical system 23 during capture of an image of a fundus to thereby set a condensing position of measurement light in the fundus Er. In this case, the control unit 70 may control the condensing position variable optical system 23 so that measurement light is first condensed at the rear side focal position Fr in the objective optical system 27. For example, the control unit 70 adjusts a refractive power of a variable focus lens (lens 23a) to a positive preset value. As a result, measurement light is collimated by the objective optical system 27, and thus the measurement light is condensed on a fundus in a case of the eye E having no refraction error. In a case where the eye E has a refraction error, the control unit 70 may offset a condensing position to that extent. Consequently, there is a tendency for a tomographic image of the fundus Er to be satisfactorily acquired.

In addition, as illustrated in FIG. 4B, the control unit 70 sets a luminous flux diameter of measurement light in a light path between the interference optical system 2 and the scanning unit 24 (in other words, an optical scanner) during capture of an image of a fundus to be larger than that during capture of an image of an anterior ocular segment. As a result, NA of measurement light which is incident on the objective optical system 27 becomes larger, and thus a high-resolution fundus tomographic image is easily obtained. Meanwhile, the depth of focus becomes smaller than that during capture of an image of an anterior ocular segment.

In this manner, in the examples of FIGS. 4A and 4B, in a case where a turning position of measurement light in the eye E is displaced to a first position, the control unit 70 generates a tomographic image W2 of an anterior ocular segment based on an output signal from the detector 40. In addition, in a case where a turning position of measurement light is displaced to a second position, the control unit 70 generates a tomographic image W1 based on an output signal from the detector 40.

Figure 3:
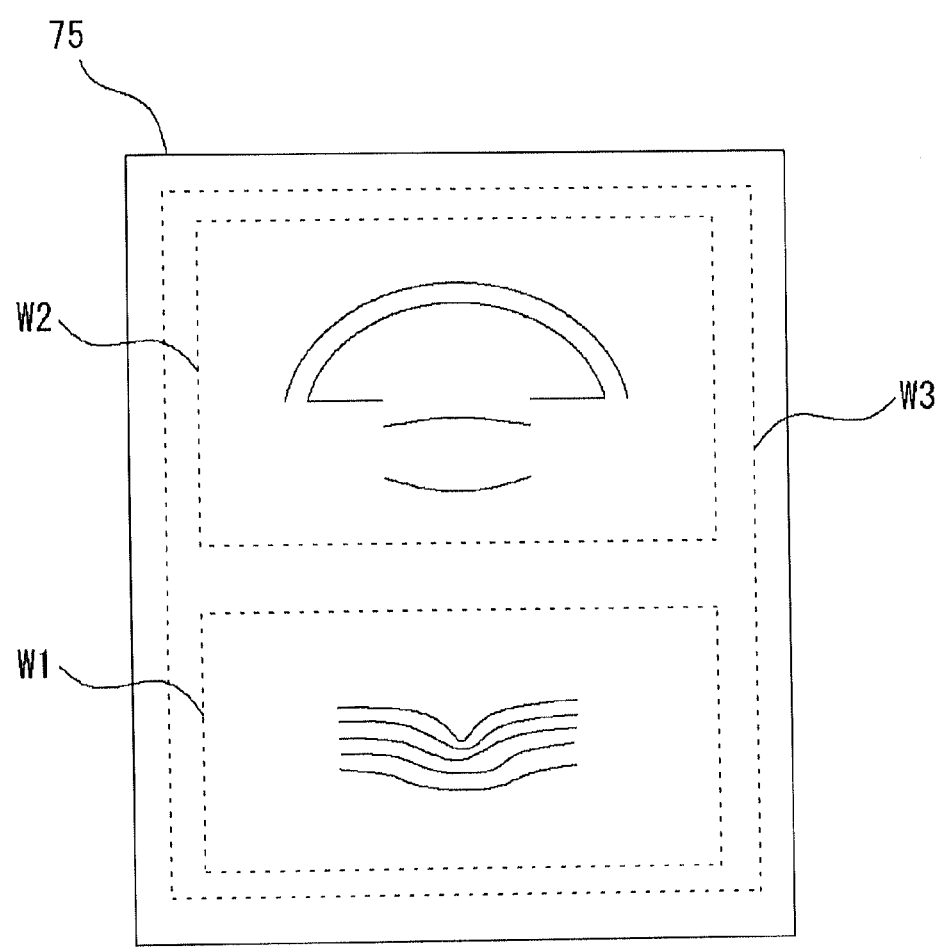
FIG. 3 is a diagram illustrating a tomographic image captured in the ophthalmic imaging device.

In a case where the tomographic image W2 of the anterior ocular segment and the tomographic image W1 of the fundus Er are generated, the control unit 70 combines the tomographic images W1 and W2 with each other based on distance information indicating a distance between depth bands corresponding to the respective tomographic images (in other words, a distance between the anterior ocular segment (first depth band) and the fundus Er (second depth band)) to thereby generate a composite image W3 (see FIG. 3). The distance information may be, for example, an average value in a human's eye or a fixed value such as a standard value, or may be a measured value in the eye E which is obtained by an eye dimension measurement apparatus such as an eye axial length measurement apparatus. In addition, the distance information may be acquired based on an output signal from the detector 40 in the OCT device 1, and the control unit 70 may generate the composite image W3 using the distance information. In addition, in FIG. 3, the composite image W3 is shown as an image including the entirety of the tomographic images W1 and W2, but is not necessarily limited thereto, and may be an image in which parts of the tomographic images W1 and W2 are combined with each other. In addition, the composite image W3 may be an image in which the tomographic images W1 and W2 are superimposed on an eyeball model image imitating an eyeball.

In addition, in the first embodiment, the relative position of the scanning unit 24 with respect to the objective optical system 27 is set to be the pupil conjugate position Ic, and thus the tomographic image W1 of the fundus Er can be captured. Therefore, when the scanning unit 24 is set at the rear side focus Fr of the objective optical system 27 in a state where the position of the objective optical system 27 is fixed, a scanning optical system constituted by the scanning unit 24 and the objective optical system 27 serves as an object-side telecentric optical system, and thus the tomographic image W2 of the anterior ocular segment can be captured. In this manner, the OCT device 1 can obtain the tomographic image W2 of the anterior ocular segment and the tomographic image W1 of the fundus Er without changing a working distance (for example, a distance between a cornea Ec of the eye E and an end on the subject side in the objective optical system 27).

In addition, in the first embodiment, the control unit 70 controls the condensing position variable optical system 23 to thereby change a condensing position of measurement light in the direction of the optical axis L1 in association with a change in the relative position of the scanning unit 24 with respect to the objective optical system 27. In more detail, the control unit 70 controls the condensing position variable optical system 23 so as to set a condensing position of measurement light to be in an image capturing depth band corresponding to the position of the scanning unit 24. That is, the control unit 70 controls the condensing position variable optical system 23 in association with the relative position of the scanning unit 24 with respect to the objective optical system 27 so that measurement light is condensed in the anterior ocular segment in a case where a turning position is displaced to a position corresponding to the anterior ocular segment and so that measurement light is condensed in the fundus Er in a case where a turning position is displaced to a position corresponding to the fundus Er. As a result, it is possible to satisfactorily obtain the tomographic images W1 and W2 in each depth band.

In addition, in the OCT device 1 of the first embodiment, the control unit 70 controls the driving unit 50 (adjuster) of the luminous flux diameter adjustment unit 22 in association with a change in the relative position of the scanning unit 24 with respect to the objective optical system 27. Thereby, the luminous flux diameter of measurement light in a light path between the interference optical system 2 and the scanning unit 24 (in other words, an optical scanner) is adjusted in accordance with the position of the scanning unit 27. As a result, as described above, in the first embodiment, a depth of focus depending on an image capturing depth band is set. Consequently, a region in which a satisfactory resolution is obtained is appropriately set for each of the tomographic images W1 and W2 in the depth direction.

Second Embodiment

Figure 5:
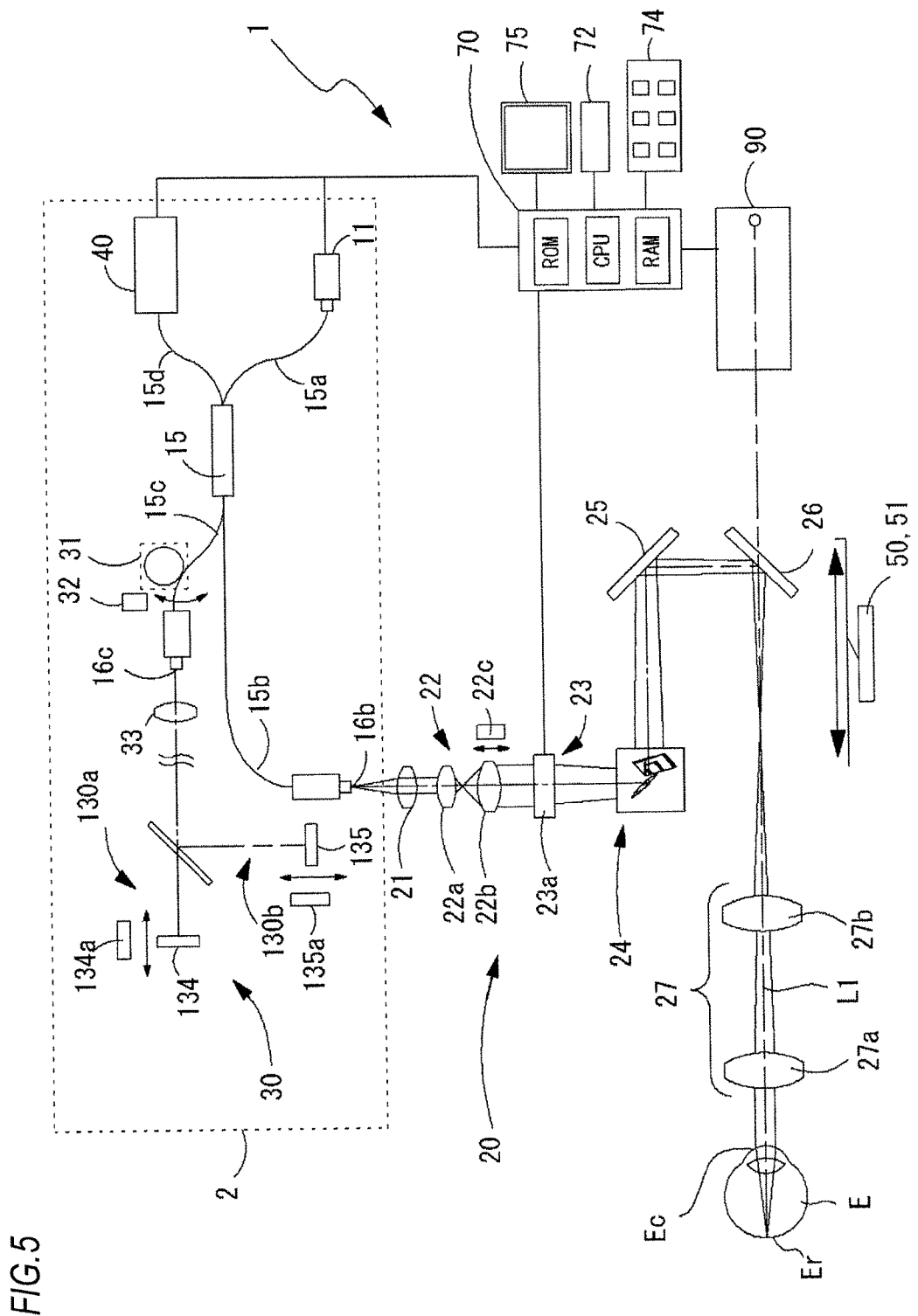
FIG. 5 is a schematic diagram illustrating a configuration of an ophthalmic imaging device according to a second embodiment.

Next, a second embodiment of the present disclosure will be described with reference to FIG. 5. Here, a description will be given with a focus on differences from the first embodiment. In addition, in the second embodiment, the same components as those in the first embodiment will be denoted by the same reference numerals and signs, and a description thereof will be omitted.

First, an optical system of an OCT device 1 according to the second embodiment will be described. In the OCT device 1 according to the second embodiment, an optical configuration of a reference optical system 30 is different from that in the first embodiment. The reference optical system 30 in the second embodiment includes a first reference light path 130a, and a second reference light path 130b having a length of a light path which is different from that of the first reference light path 130a. For example, as illustrated in FIG. 5, a light path of the reference optical system 30 is branched into the first reference light path 130a and the second reference light path 130b by a light branching member 131 (for example, a half mirror or the like). In addition, reference mirrors 134 and 135 are disposed at the first reference light path 130a and the second reference light path 130b, respectively. In addition, as illustrated in FIG. 5, the reference optical system 30 may include driving units 134a and 135a that displace the positions of the respective reference mirrors 134 and 135 along an optical axis direction in order to independently adjust the lengths of the first reference light path 130a and the second reference light path 130b.

The reference optical system 30 simultaneously guides first reference light having passed through the first reference light path 130a and second reference light having passed through the second reference light path to a detector 40. In the example of FIG. 5, the first reference light is reference light which is split by a coupler 15 and then passes through the first reference light path 130a, and the second reference light is reference light which is split by the coupler 15 and then passes through the second reference light path 130b. When the first reference light and the second reference light are generated, a control unit 70 controls the driving unit 134a so that one reference mirror 134 is disposed at a position having a length of a light path corresponding to an anterior ocular segment. In more detail, the reference mirror 134 is disposed at a position in which the length of the first reference light path 130a becomes equal to the length of a light path of return light of measurement light from the anterior ocular segment. As a result, interference light of the return light from the anterior ocular segment and the first reference light generated by the first reference light path 130a is received by the detector 40. In addition, the control unit 70 controls the driving unit 135a so that the other reference mirror 135 is disposed at a position having a length of a light path which corresponds to a fundus Er. In more detail, the reference mirror 135 is disposed at a position in which the length of the second reference light path 130b becomes equal to the length of a light path of return light of measurement light from the fundus Er. As a result, interference light of the return light from the fundus Er and the second reference light generated by the second reference light path 130b is received by the detector 40. A difference in length between the first reference light path 130a and the second reference light path 130b is set to be a length depending on an interval between the fundus Er and the anterior ocular segment in a case where the first reference light and the second reference light are simultaneously generated. In the present embodiment, distance information indicating a difference in length between the first reference light path 130a and the second reference light path 130b is stored in a storage unit 72 by the control unit 70.

Next, operations of the OCT device 1 in the second embodiment will be described.

In the OCT device 1 according to the second embodiment, an output signal from the detector 40 may be processed in a state where the relative position of a scanning unit 24 with respect to an objective optical system 27 is maintained constant, so that the control unit 7 may simultaneously generate tomographic images in two depth bands. In addition, the output signal at this time is processed, so that the control unit 70 may acquire information (referred to as dimension information) regarding the dimension of the eye E which extends over two or more depth bands. In this case, as an example of the dimension information, eye axis length information can be acquired. For example, the control unit 70 controls the driving unit 50 so that the scanning unit 24 may be disposed at a rear side focal position Fr of the objective optical system 27. In this state, the control unit 70 performs Fourier transform on an interference signal which is output from the detector 40. The distribution of intensity of the interference signal after the Fourier transform is illustrated in FIG. 6.

Figure 6:
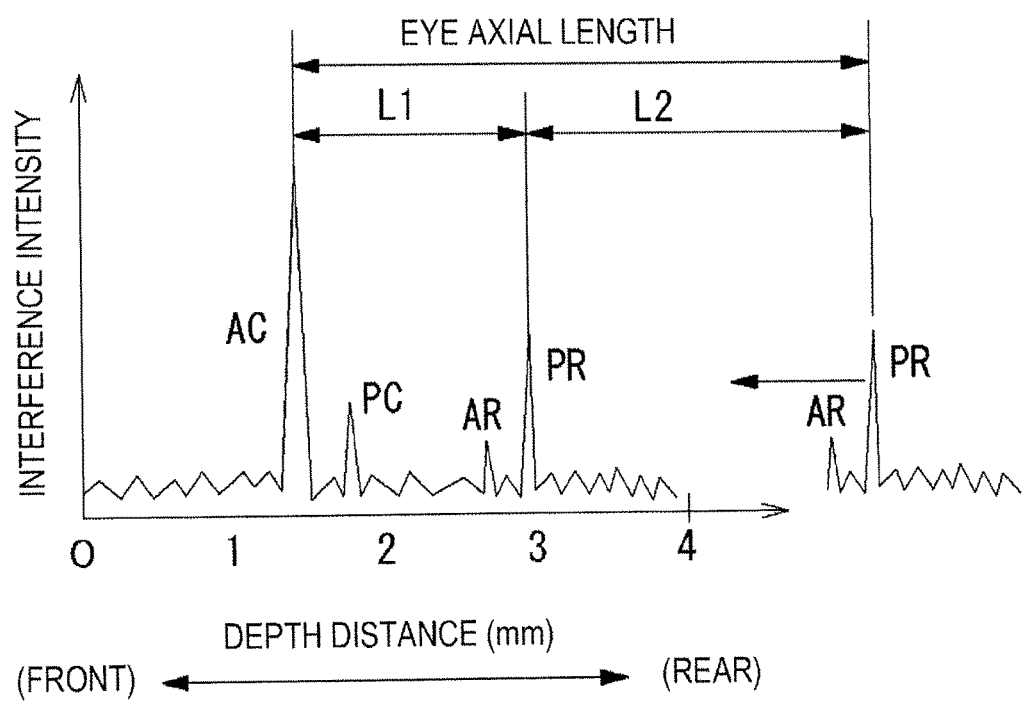
FIG. 6 is a diagram illustrating the distribution of intensity after Fourier transform in an interference signal generated by return light of measurement light from an anterior ocular segment and reference light and in an interference signal generated by return light of measurement light from a fundus and reference light.

In the distribution of intensity illustrated in FIG. 6, AC denotes an interference signal due to return light from the front surface of a cornea. PC denotes an interference signal due to return light from a fundus Er. The control unit 70 obtains an eye axis length value of the eye E from a difference between pieces of positional information respectively indicated by the interference signal AC and the interference signal PR and a value of a difference in length between the first reference light path 130*a* and the second reference light path 130*b*. For example, the control unit 70 obtains a dimension L1 between the interference signal AC and the interference signal PR in the depth direction. In addition, a difference L2 in length between the first reference light path 130*a* and the second reference light path 130*b* which is stored in advance in the storage unit 72 is added to the dimension L1. Thereby, it is possible to obtain an eye axis length of the eye E (eye axis length=L1+L2).

In addition, an interference signal (peak) is obtained due to reflection from a position other than the front surface of the cornea and the fundus Er. The control unit 70 may process the interference signal to thereby obtain dimension information regarding the depth direction.

Third Embodiment

Next, a third embodiment in the present disclosure will be described. Here, a description will be given with a focus on differences from the first and second embodiments. In addition, in the third embodiment, the same components as those in the first embodiment will be denoted by the same reference numerals and signs, and a description thereof will be omitted. An OCT device 1 according to the third embodiment includes an SS-OCT optical system. In other words, an interference optical system 2 is replaced with an SS-OCT optical system including a wavelength sweeping light source that temporally sweeps an emission wavelength. In addition, a light source 11 is replaced with a wavelength sweeping type light source. Further, a detector 40 may be replaced with a balance detector constituted by a light receiving element. For example, a point sensor having one light receiving unit may be used as the light receiving element. An avalanche photodiode or the like may be used as the light receiving element. In this case, the control unit 70 samples an interference signal of measurement light and reference light in accordance with a change in emission wavelength due to the wavelength sweeping light source to thereby obtain a tomographic image of an object to be examined based on interference signals obtained in respective wavelengths which are obtained by the sampling. For a more detailed method of processing an interference signal in SS-OCT and method of acquiring depth information, see, for example, JP-A-2015-068775.

In a case of SS-OCT, sensitivity is less reduced in a deep portion than in a case of SD-OCT. For this reason, as a result of sampling, an interference signal due to return light from a wide depth band (for example, between an anterior ocular segment and a fundus Er) is easily acquired. For this reason, even when the length of a light path of a reference optical system 30 is not changed and even when two or more types of reference light (for example, first reference light and second reference light) having different phases are not generated by the reference optical system 30, it is possible to obtain an interference signal due to return light from a wide depth band. Meanwhile, in this case, it is preferable that the length of a light path of the reference optical system 30 is set to be, for example, an intermediate length between the length of a light path of return light from an anterior ocular segment and the length of a light path of return light from a fundus Er. In this case, similarly to the second embodiment, the OCT device 1 according to the third embodiment may acquire dimension information of the eye E based on an interference signal which is sampled in a state where a scanning unit 24 is maintained constant. However, in the third embodiment, the length of a light path of reference light is constant. Accordingly, regarding dimension information (typically, an eye axis length) between the fundus E and the anterior ocular segment, a dimension in the depth direction from an interference signal due to return light from the front surface of the cornea to an interference signal due to return light from the fundus Er can be obtained as the dimension information.

Meanwhile, similarly to the first embodiment, the OCT devices 1 of the second and third embodiments may displace a turning position of measurement light in a direction of an optical axis L1 to thereby obtain tomographic images of different depth bands for each turning position. In addition, at this time, as described in the first embodiment, at least one of the luminous flux diameter of measurement light in a light path between the interference optical system 2 and the scanning unit 24 (in other words, an optical scanner) and a condensing position of the measurement light may be adjusted in association with switching of the position of the scanning unit 24.

Modification Example

As described above, a description has been given based on the embodiments, but the present disclosure is not limited to the above-described embodiments, but extends to examples in which the above-described embodiments are modified in various ways. Further, the above embodiments and the examples may be arbitrary combined to carry out the aspect of the present invention.

For example, in the above-described embodiments, as a specific example having a configuration in which the relative position of a scanning unit 24 with respect to an objective optical system 27 in a direction of an optical axis L1 is switched, a configuration in which a light path between the objective optical system 27 and the scanning unit 24 is changed is described. However, the present disclosure is not necessarily limited thereto.

Figure 7:
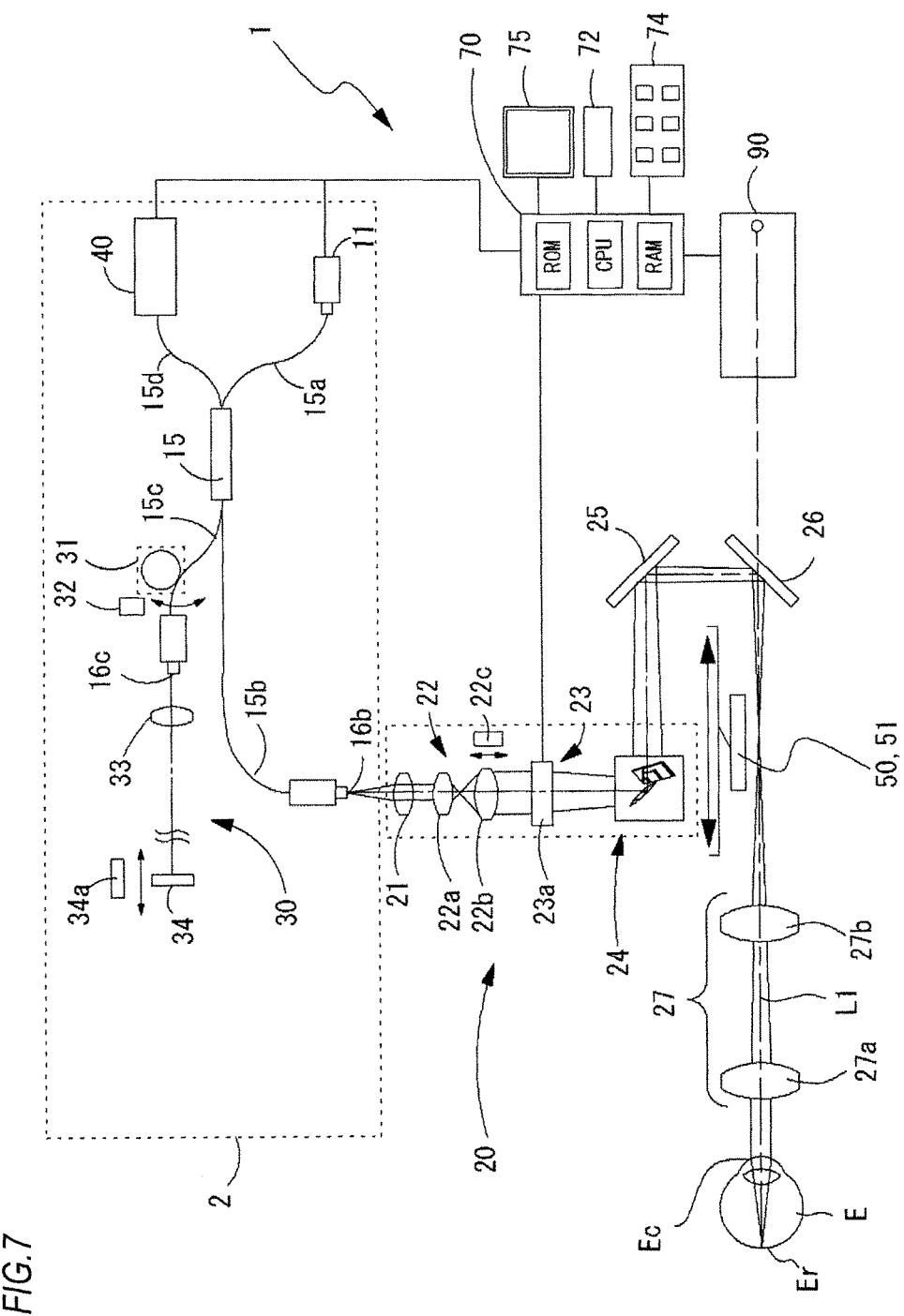
FIG. 7 is a schematic diagram of an ophthalmic imaging device which is configured to adjust the relative position of a scanning unit with respect to an objective optical system, according to a first modification example.

For example, as illustrated in FIG. 7, at least the scanning unit 24 (in other words, an optical scanner) is displaced in the direction of the optical axis L1 by controlling the driving of a driving unit 50 by a control unit 70, so that the relative position of the scanning unit 24 with respect to the objective optical system 27 may be displaced. In the example of FIG. 7, the driving unit 50 moves units ranging from an end 16*b* of a fiber 15*b* to the scanning unit 24 in the horizontal direction of the paper of FIG. 7. Meanwhile, a configuration in which a relative position is displaced by moving the scanning unit 24 is not limited thereto. For example, a mechanism that integrally moves the scanning unit 24 and a mirror 25 in an optical axis direction (for example, the vertical direction of the paper of FIG. 1A) of measurement light from a lens 23a may be included as the driving unit 50.

Figure 8A:
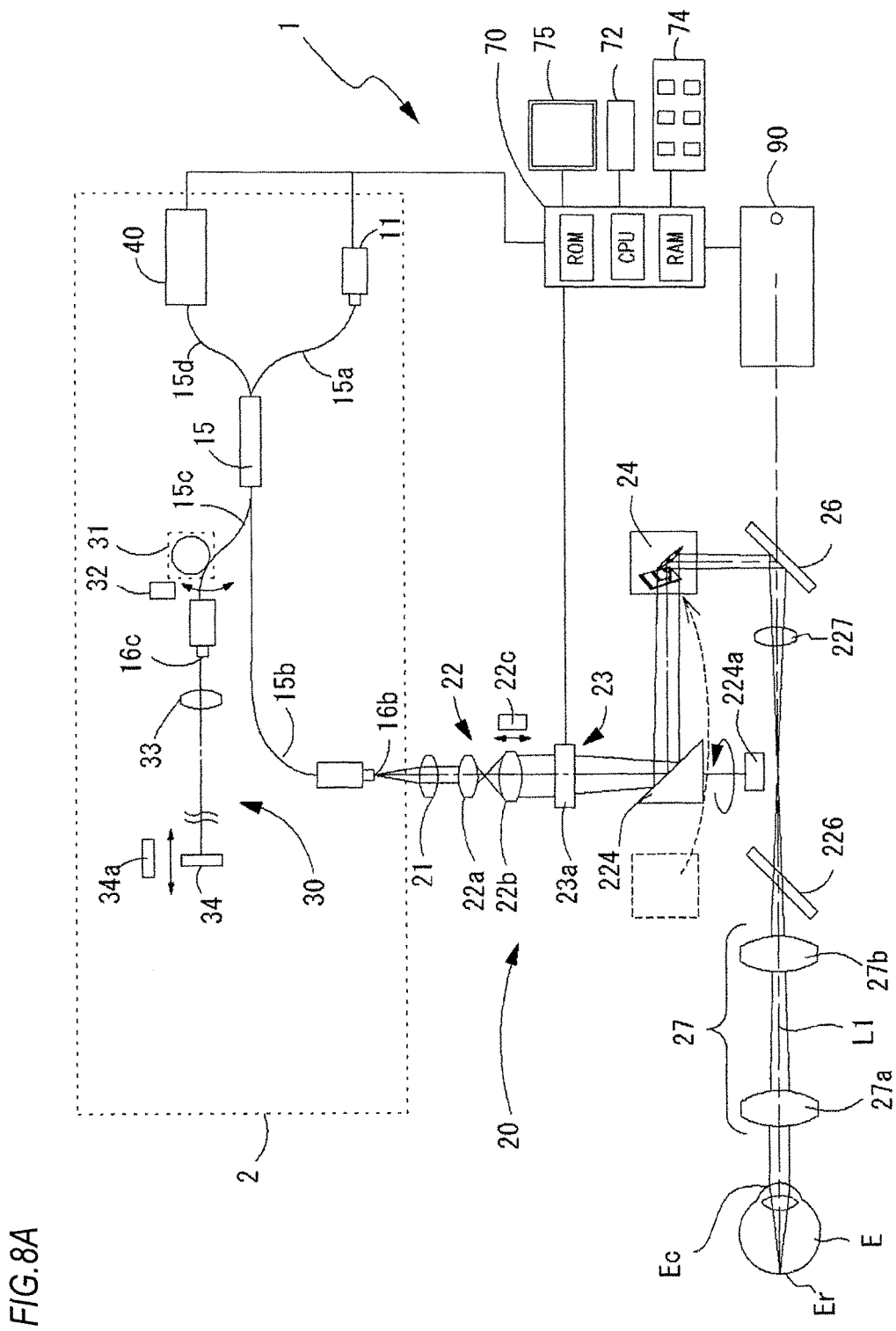
FIG. 8A is a schematic diagram of an ophthalmic imaging device which is configured to adjust the relative position of a scanning unit with respect to an objective optical system, according to a second modification example, and illustrates an optical arrangement during capture of an image of a fundus.
Figure 8B:
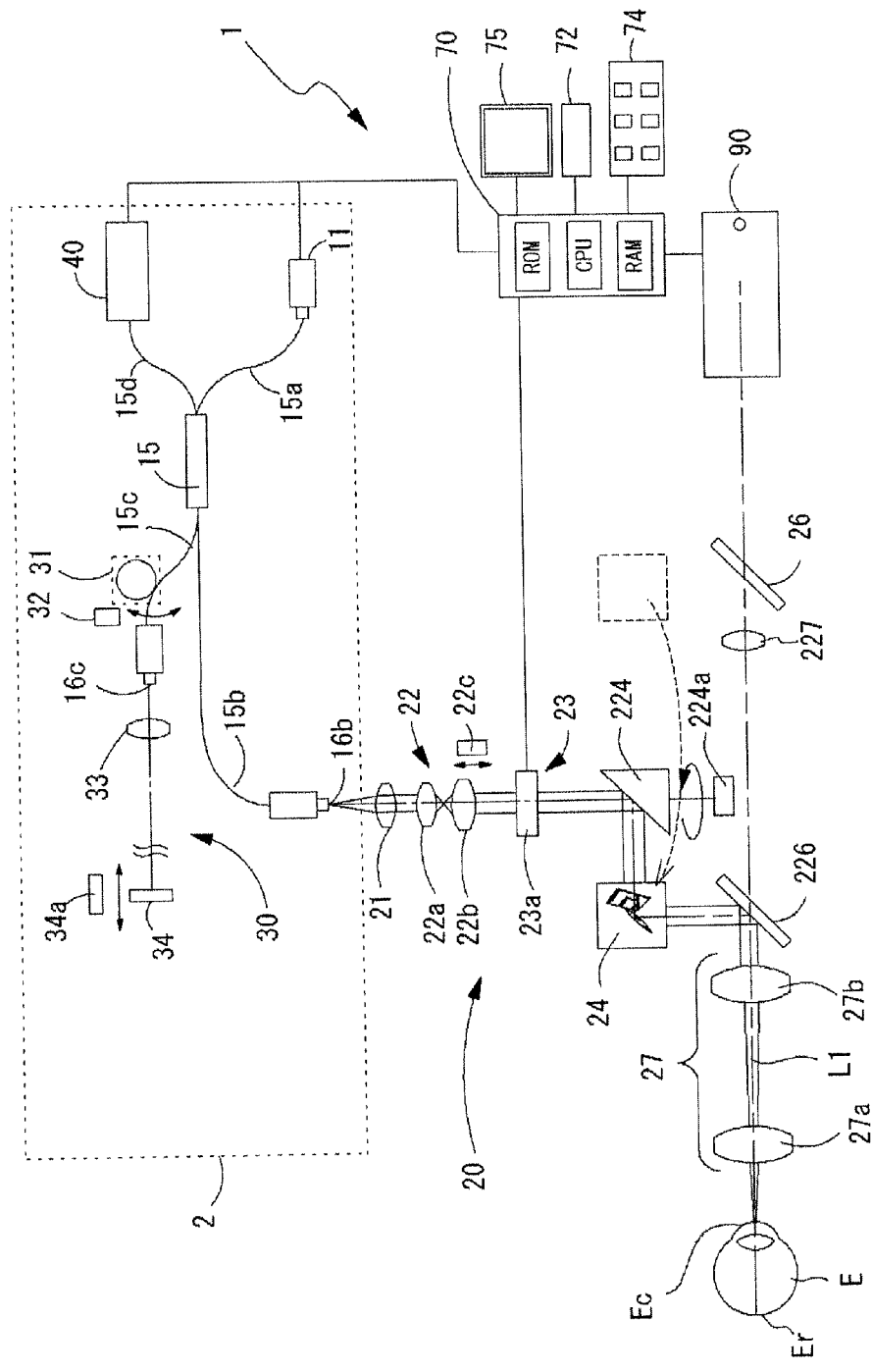
FIG. 8B is a schematic diagram of the ophthalmic imaging device which is configured to adjust the relative position of the scanning unit with respect to the objective optical system, according to the second modification example, and illustrates an optical arrangement during capture of an image of an anterior ocular segment.

In addition, a configuration in which the relative position of the scanning unit 24 with respect to the objective optical system 27 in an optical axis direction may be a configuration in which a light path between the objective optical system 27 and the optical scanner 24 is switched. For example, in examples of FIGS. 8A and 8B, a mirror 224 rotating around its optical axis by the driving of a motor 224a (a portion of a driving unit) is provided on an emission side of the lens 23a. The mirror 224 is disposed so as to be inclined with respect to an incident optical axis of measurement light. In addition, an actuator (a portion of a driving unit), not shown in the drawing, for disposing the scanning unit 24 in a reflection direction of the mirror 224 is provided, and thus the entire scanning unit 24 is moved in association with the rotation of the mirror 224. The mirror 224 and the scanning unit 24 move in association with each other, and thus a light path between the objective optical system 27 and the scanning unit 24 is switched to a first light path (see FIG. 8A) including a dichroic mirror 26 and a lens 227 and a second light path (see FIG. 8B) including a half mirror 27. For example, the relative position of the scanning unit 24 with respect to the objective optical system 27 in an optical axis direction may be changed by the switching of the light path. Meanwhile, in the examples of FIGS. 8A and 8B, the lens 227 of which the relative position with respect to the objective optical system 27 is fixed is provided, and a turning position of measurement light in the eye E is set to a pupil conjugate position in a case where irradiation with measurement light is performed through the first light path including the lens 227. On the other hand, in a case where irradiation with measurement light is performed through the second light path that does not include the lens 227, a turning position of measurement light in the eye E is set to an infinite point. An optical member included in only one of the first light path and the second light path is not limited to a lens, and may be a beam expander or the like or may be any one other than those. A configuration in which a light path between the objective optical system 27 and the optical scanner 24 is switched is not limited to those illustrated in FIGS. 8A and 8B. For example, a configuration may be adopted in which measurement light is guided to a different light path by switching a swing angle of measurement light in the scanning unit 24.

Figure 9A:
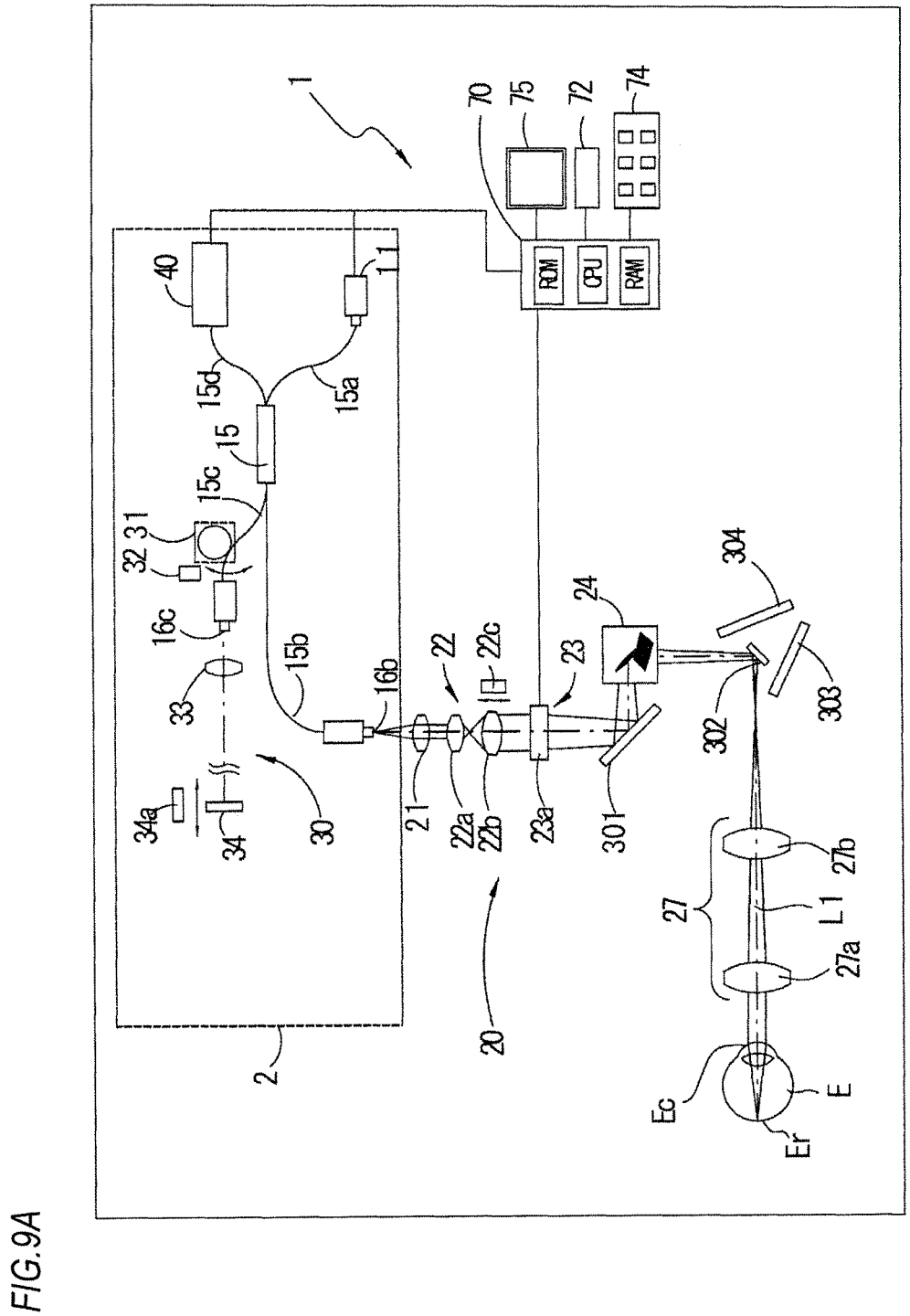
FIG. 9A is a schematic diagram of an ophthalmic imaging device which is configured to adjust the relative position of a scanning unit with respect to an objective optical system, according to a third modification example, and illustrates an optical arrangement during capture of an image of a fundus.
Figure 9B:
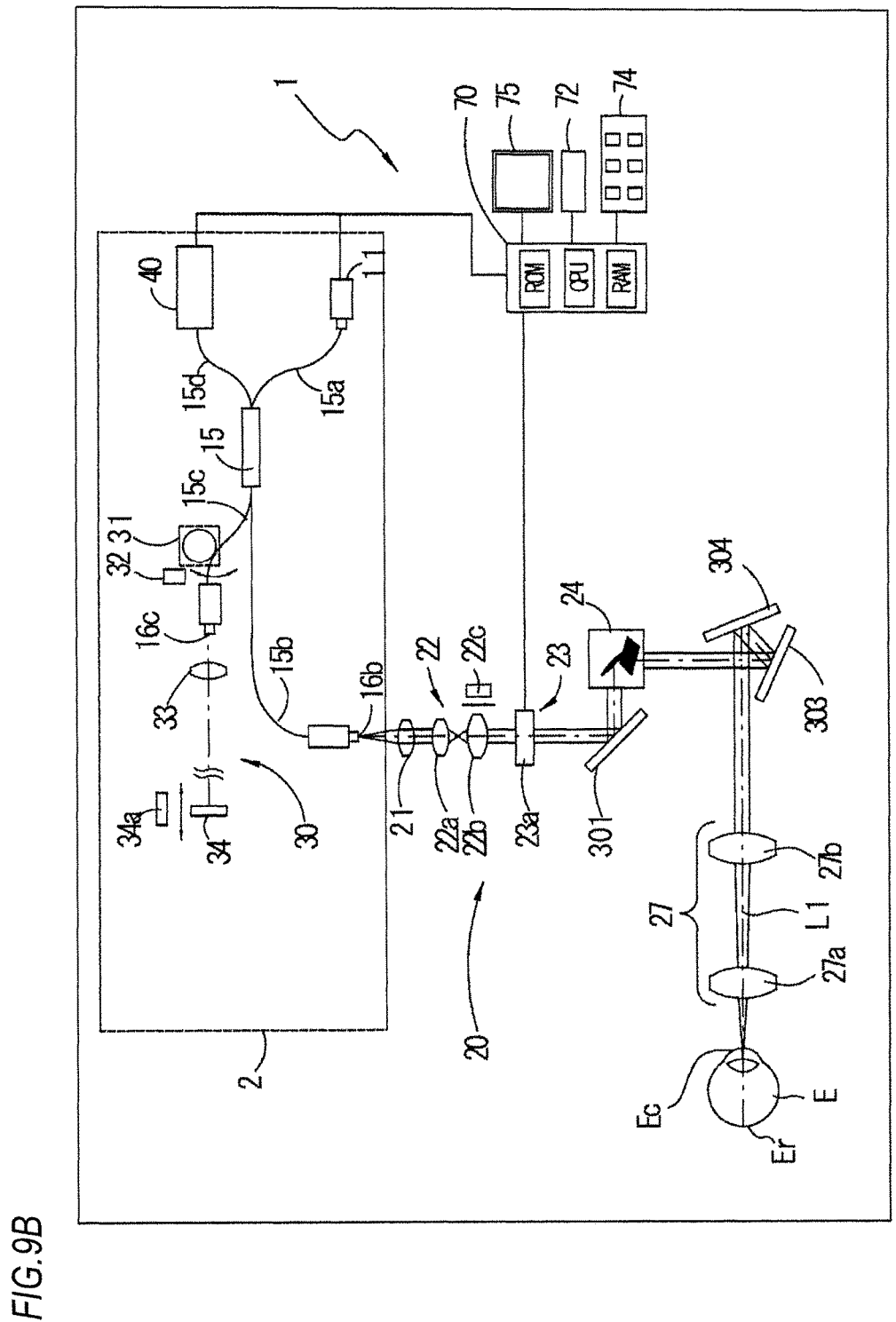
FIG. 9B is a schematic diagram of the ophthalmic imaging device which is configured to adjust the relative position of the scanning unit with respect to the objective optical system, according to the third modification example, and illustrates an optical arrangement during capture of an image of an anterior ocular segment.

In addition, for example, a configuration may be adopted in which an optical member (for example, any of a lens, a mirror, and the like) capable of being inserted and removed by an inserting and removing mechanism (this is one example of the driving unit) is provided in a light path between the objective optical system 27 and the scanning unit 24 and the control unit 70 switches between a state where the optical member is inserted into the light path and a state where the optical member is not inserted into the light path by the driving control of the inserting and removing mechanism to thereby switch the relative position of the scanning unit 24 with respect to the objective optical system 27. For example, in examples of FIGS. 9A and 9B, a relative position between the scanning unit 24 and the objective optical system 27 is switched by the insertion and removal of a mirror 302. Meanwhile, in FIGS. 9A and 9B, an inserting and removing mechanism of the mirror 302 is not shown. For example, the mirror 302 may move in a direction perpendicular to the paper of FIGS. 9A and 9B so that the insertion and removal of measurement light into and from a light path are performed. As illustrated in FIG. 9B, in a state where the mirror 302 is retreated from a light path of measurement light, measurement light from the scanning unit 24 is guided to the objective optical system 27 through mirrors 303 and 304. On the other hand, as illustrated in FIG. 9A, in a state where the mirror 302 is inserted into a light path of measurement light, reflection by the mirrors 303 and 304 is omitted with respect to FIG. 9B, and measurement light from the scanning unit 24 is guided to the objective optical system 27. In other words, the length of a light path of measurement light between the scanning unit 24 and the objective optical system 27 is switched by the insertion and removal of the mirror 302.

In addition, in the above-described embodiments, a description has been given of a case where a first depth band is set to be an anterior ocular segment and a second depth band is set to be a fundus Er and tomographic images in the respective depth bands are obtained. However, the first depth band and the second depth band may be different regions in the depth direction of the eye E and are not necessarily limited thereto. For example, the first depth band may be a front portion of the anterior ocular segment, and the second depth band may be a rear portion of the anterior ocular segment. In a case where a tomographic image in the front portion of the anterior ocular segment is captured, for example, the control unit 70 may displace the relative position of the scanning unit 24 with respect to the objective optical system 27 to a rear side focal position Fr of the objective optical system 27 (at this time, a turning position of measurement light which is formed on a side closer to the eye than the scanning unit 24 is considered to be an infinite point). In this case, the control unit 70 may generate a tomographic image in the front portion of the anterior ocular segment based on an output signal from a detector 40. In addition, in a case where a tomographic image in the rear portion of the anterior ocular segment is captured, the control unit 70 may form the relative position of the scanning unit 24 with respect to the objective optical system 27 at a position separated from a rear side focal position Fr (and a conjugate position of the rear side focal position Fr) of the objective optical system 27. Thereby, for example, a turning position may be displaced into the eye. In this case, the control unit 70 may generate a tomographic image in the rear portion of the anterior ocular segment based on an output signal from the photodetector 40.

In addition, in the above-described embodiments, a description has been given of a case where the scanning unit 24 is switched at two positions with respect to the objective optical system 27 so that tomographic images in two depth bands (an anterior ocular segment and a fundus Er) are obtained at the respective positions. However, an OCT device 1 may be configured such that the position of the scanning unit 24 is switched at three or more positions to thereby obtain tomographic images in three or more depth bands based on interference signals at the respective positions. In addition, either one or both of a condensing position of measurement light and a luminous flux diameter between the OCT optical system 2 and the scanning unit 24 may be adjusted for each position of the scanning unit 24 by either one or both of a condensing position variable optical system 23 and a luminous flux diameter adjustment unit 22.

In addition, the control unit 70 may change a condensing position which is set by the condensing position variable optical system 23 in accordance with a scanning position of measurement light. For example, the control unit 70 may change a refractive power of the lens 23a in accordance with the shape of an anterior ocular segment. For example, the anterior ocular segment is a curved surface projecting to an objective lens side, and thus measurement light may be condensed at a position farther away from an objective lens in a case where a peripheral portion of the cornea is scanned than in a case where a central portion of the cornea is scanned. For example, the control unit 70 may reduce a refractive power of a refractive power variable unit so that measurement light is condensed at a position separated from the objective lens. In this manner, a condensing position of measurement light is adjusted in accordance with a scanning position of the measurement light, and thus the measurement light can allow a more accurate tomographic image of the anterior ocular segment to be acquired.

In addition, an embodiment of the present disclosure may be the following first and second ophthalmic imaging devices.

The first ophthalmic imaging device, which is an ophthalmic imaging device for capturing a tomographic image of the eye, includes an OCT optical system that detects interference of reference light and measurement light with which the eye is irradiated, by a photodetector, a measurement optical system that includes an optical scanner which deflects the measurement light from the OCT optical system in order to perform scanning with the measurement light and an objective optical system which is disposed between the optical scanner and the eye and guides the measurement light deflected by the optical scanner to the eye, a driving unit that drives an optical member included in the measurement optical system in order to at least change a depth band of the eye, of which the tomographic image is captured, between a first depth band and a second depth band, a luminous flux diameter adjustment unit for changing a luminous flux diameter of measurement light in a light path between the OCT optical system and the optical scanner, and a control unit that controls the luminous flux diameter adjustment unit and the driving unit to thereby adjust the luminous flux diameter in accordance with a depth band of which internal information is obtained.

In the second ophthalmic imaging device, in a case where the first depth band is an anterior ocular segment and the second depth band is a fundus, the control unit adjusts the luminous flux diameter to a first luminous flux diameter in a case where the optical scanner is disposed at the first position, and adjusts the luminous flux diameter to a second luminous flux diameter larger than the first luminous flux diameter in a case where the optical scanner is disposed at the second position.

What is claimed is:

1. An ophthalmic imaging device for capturing a tomographic image of an eye, the ophthalmic imaging device comprising:
   an OCT optical system including a photodetector configured to detect interference of reference light and measurement light with which the eye is irradiated;
   a measurement optical system including an optical scanner and an objective optical system, the optical scanner being configured to deflect the measurement light emitted from the OCT optical system to perform scanning with the measurement light, and the objective optical system being disposed between the optical scanner and the eye and configured to guide the measurement light deflected by the optical scanner to the eye;
   a driver configured to displace a relative position of the optical scanner with respect to the objective optical system in an optical axis direction; and
   a controller configured to control the driver to adjust a turning position of the measurement light in the optical axis direction, wherein
   the controller changes the turning position between a first position corresponding to a first depth band of the eye and a second position corresponding to a second depth band of the eye which is different from the first depth band,
   the measurement optical system includes a condensing position variable optical system configured to switch a condensing position of the measurement light in the optical axis direction, and
   the controller controls the condensing position variable optical system in association with the relative position of the optical scanner in such a manner that the measurement light is condensed in the first depth band in a case where the turning position is displaced to the first position and in such a manner that the measurement light is condensed in the second depth band in a case where the turning position is displaced to the second position.

2. The ophthalmic imaging device according to claim 1, wherein
   the first depth band is an anterior ocular segment, and the second depth band is a fundus, and
   the ophthalmic imaging device further comprises an image processor configured to generate a tomographic image of the anterior ocular segment based on an output signal from the photodetector in a case where the turning position is displaced to the first position and generate a tomographic image of the fundus based on an output signal from the photodetector in a case where the turning position is displaced to the second position.

3. The ophthalmic imaging device according to claim 1, wherein
   the first depth band is a front portion of the anterior ocular segment, and the second depth band is a rear portion of the anterior ocular segment, and
   the ophthalmic imaging device further comprises an image processor configured to generate a tomographic image in a front portion of the anterior ocular segment based on an output signal from the photodetector in a case where the turning position is displaced to the first position and generate a tomographic image in a rear portion of the anterior ocular segment based on an output signal from the photodetector in a case where the turning position is displaced to the second position.

4. The ophthalmic imaging device according to claim 3, wherein
   in a case where the tomographic image in the first depth band and the tomographic image in the second depth band are generated, the image processor combines the tomographic image in the first depth band and the tomographic image in the second depth band based on distance information indicating a distance between the first depth band and the second depth band to generate a composite image.

5. The ophthalmic imaging device according to claim 2, wherein
   in a case where the turning position is switched between the first position and the second position, the controller controls the driver to displace the relative position of the optical scanner in such a manner that switching is performed between even and odd numbers of pupil images of the eye which are formed in a section between the optical scanner and an end on a subject side in the objective optical system or between even and odd numbers of Fourier transformed images of the pupil which are formed in the section between the optical scanner and the end of the subject side in the objective optical system.

6. The ophthalmic imaging device according to claim 2, wherein
the controller controls the driver to dispose the relative position of the optical scanner at a rear side focal position in the objective optical system or a conjugate position of the rear side focal position in a case where the turning position is displaced to the first position, and dispose the relative position of the optical scanner at a pupil conjugate position to the eye with respect to the objective optical system in a case where the turning position is displaced to the second position.

7. The ophthalmic imaging device according to claim 1, wherein
the condensing position variable optical system includes at least one lens, and is configured to change at least any of refraction of the lens and a positional relationship between the objective optical system and the lens to switch the condensing position of the measurement light in the optical axis direction.

8. The ophthalmic imaging device according to claim 1, wherein
the measurement optical system includes a luminous flux diameter adjuster which is disposed in a light path between the OCT optical system and the optical scanner and is configured to change a luminous flux diameter of measurement light in the light path, and
the controller controls the luminous flux diameter adjuster to adjust the luminous flux diameter in accordance with a position of the optical scanner.

9. The ophthalmic imaging device according to claim 8, wherein
the first depth band is an anterior ocular segment and the second depth band is a fundus, and
the controller controls the luminous flux diameter adjuster to adjust the luminous flux diameter to a first luminous flux diameter if the turning position is displaced to the first position and adjust the luminous flux diameter to a second luminous flux diameter larger than the first luminous flux diameter if the turning position is displaced to the second position.

10. The ophthalmic imaging device according to claim 8, wherein the luminous flux diameter adjuster includes at least one of an aperture capable of being inserted into and removed from the light path by an inserting and removing mechanism, a variable aperture capable of changing a size of an opening, and a variable beam expander.

11. The ophthalmic imaging device according to claim 1, wherein the driver changes a length of a light path between the objective optical system and the optical scanner to thereby displace a relative position of the optical scanner.

12. The ophthalmic imaging device according to claim 1, further comprising:
an optical member of which a relative position with respect to the objective optical system is fixed,
wherein the driver is configured to switch a light path between the objective optical system and the optical scanner to a first light path that includes the optical member and a second light path that does not include the optical member,
wherein the turning position is set to one of the first position and the second position by the light path being set to the first light path, and wherein the turning position is set to the other one of the first position and the second position by the light path being set to the second light path.

13. The ophthalmic imaging device according to claim 1, wherein
the driver moves the optical scanner in the optical axis direction to displace the relative position of the optical scanner.

14. The ophthalmic imaging device according to claim 1, further comprising:
a reference optical system configured to guide the reference light to the photodetector, the reference optical system including a light path length adjustment unit configured to adjust a length of a light path of the reference light,
wherein the controller controls the light path length adjustment unit to adjust the length of the light path of the reference light in accordance with the relative position of the optical scanner.

15. The ophthalmic imaging device according to claim 1, further comprising:
a reference optical system configured to guide the reference light, the reference optical system including a branching unit configured to branch and guide the reference light into a first reference light path and a second reference light path having a length of a light path which is different from that of the first reference light path, and simultaneously guide first reference light which is the reference light having passed through the first reference light path and second reference light which is the reference light having passed through the second reference light path to the photodetector.

16. The ophthalmic imaging device according to claim 1, wherein
the OCT optical system is an SS-OCT optical system that includes a wavelength sweeping light source temporally sweeping an emission wavelength.

17. An ophthalmic imaging device for capturing a tomographic image of an eye, the ophthalmic imaging device comprising:
an OCT optical system including a photodetector configured to detect interference of reference light and measurement light with which the eye is irradiated;
a measurement optical system including an optical scanner and an objective optical system, the optical scanner being configured to deflect the measurement light emitted from the OCT optical system to perform scanning with the measurement light, and the objective optical system being disposed between the optical scanner and the eye and configured to guide the measurement light deflected by the optical scanner to the eye;
a driver configured to displace a relative position of the optical scanner with respect to the objective optical system in an optical axis direction; and
a controller configured to control the driver to adjust a turning position of the measurement light in the optical axis direction,
wherein the controller changes the turning position between a first position corresponding to a first depth band of the eye and a second position corresponding to a second depth band of the eye which is different from the first depth band,
the first depth band is an anterior ocular segment and the second depth band is a fundus,
the measurement optical system includes a luminous flux diameter adjuster which is disposed in a light path between the OCT optical system and the optical scanner and is configured to change a luminous flux diameter of measurement light in the light path, and the controller controls the luminous flux diameter adjuster to adjust the luminous flux diameter in accordance with a position of the optical scanner, adjust the luminous flux diameter to a first luminous flux diameter if the turning position is displaced to the first position, and adjust the luminous flux diameter to a second luminous flux diameter larger than the first luminous flux diameter if the turning position is displaced to the second position.

18. The ophthalmic imaging device according to claim 17, wherein the luminous flux diameter adjuster includes at least one of an aperture capable of being inserted into and removed from the light path by an inserting and removing mechanism, a variable aperture capable of changing a size of an opening, and a variable beam expander.

19. An ophthalmic imaging device for capturing a tomographic image of an eye, the ophthalmic imaging device comprising:

an OCT optical system including a photodetector configured to detect interference of reference light and measurement light with which the eye is irradiated;

a measurement optical system including an optical scanner and an objective optical system, the optical scanner being configured to deflect the measurement light emitted from the OCT optical system to perform scanning with the measurement light, and the objective optical system being disposed between the optical scanner and the eye and configured to guide the measurement light deflected by the optical scanner to the eye;

a driver configured to displace a relative position of the optical scanner with respect to the objective optical system in an optical axis direction;

a controller configured to control the driver to adjust a turning position of the measurement light in the optical axis direction, wherein the controller changes the turning position between a first position corresponding to a first depth band of the eye and a second position corresponding to a second depth band of the eye which is different from the first depth band; and a reference optical system configured to guide the reference light, the reference optical system including a branching unit configured to branch and guide the reference light into a first reference light path and a second reference light path having a length of a light path which is different from that of the first reference light path, and simultaneously guide first reference light which is the reference light having passed through the first reference light path and second reference light which is the reference light having passed through the second reference light path to the photodetector.

* * * * *